(12) United States Patent
Dalal et al.

(10) Patent No.: US 9,332,913 B2
(45) Date of Patent: May 10, 2016

(54) SYSTEM AND METHOD FOR DISCRIMINATING HYPERVOLEMIA, HYPERVOLEMIA AND EUVOLEMIA USING AN IMPLANTABLE MEDICAL DEVICE

(75) Inventors: Yousuf Dalal, Porter Ranch, CA (US); Stuart Rosenberg, Castaic, CA (US)

(73) Assignee: PACESETTER, INC., Sylmar, CA (US)

( * ) Notice: Subject to any disclaimer, the term of this patent is extended or adjusted under 35 U.S.C. 154(b) by 989 days.

(21) Appl. No.: 13/333,777

(22) Filed: Dec. 21, 2011

(65) Prior Publication Data

US 2013/0165802 A1    Jun. 27, 2013

(51) Int. Cl.
| | | |
|---|---|---|
| A61B 5/02 | (2006.01) |
| A61B 5/0215 | (2006.01) |
| A61N 1/365 | (2006.01) |
| A61B 5/00 | (2006.01) |
| A61N 1/39 | (2006.01) |

(52) U.S. Cl.
CPC ............. *A61B 5/0215* (2013.01); *A61B 5/7239* (2013.01); *A61B 5/7257* (2013.01); *A61N 1/365* (2013.01); *A61N 1/36564* (2013.01); *A61N 1/3962* (2013.01)

(58) Field of Classification Search
CPC combination set(s) only.
See application file for complete search history.

(56) References Cited

U.S. PATENT DOCUMENTS

| | | |
|---|---|---|
| 5,328,460 A | 7/1994 | Lord et al. |
| 6,480,733 B1 | 11/2002 | Turcott |
| 6,572,557 B2 | 6/2003 | Tchou et al. |
| 6,643,548 B1 | 11/2003 | Mai et al. |
| 6,666,826 B2 | 12/2003 | Salo et al. |
| 6,741,885 B1 | 5/2004 | Park et al. |
| 6,748,261 B1 | 6/2004 | Kroll et al. |
| 6,970,742 B2 | 11/2005 | Mann et al. |
| 7,137,953 B2 | 11/2006 | Eigler et al. |
| 7,195,594 B2 | 3/2007 | Eigler et al. |
| 7,272,443 B2 | 9/2007 | Min et al. |
| 7,445,605 B2 | 11/2008 | Overall et al. |
| 7,460,909 B1 | 12/2008 | Koh et al. |
| 7,483,743 B2 | 1/2009 | Mann et al. |
| 7,574,255 B1 | 8/2009 | Min |
| 7,621,036 B2 | 11/2009 | Cros et al. |
| 7,621,879 B2 | 11/2009 | Eigler et al. |
| 7,628,757 B1 | 12/2009 | Koh |
| 7,648,464 B1 * | 1/2010 | Gill et al. ...................... 600/508 |
| 7,717,854 B2 | 5/2010 | Mann et al. |
| 7,774,055 B1 | 8/2010 | Min |
| 7,794,404 B1 | 9/2010 | Gutfinger et al. |
| 7,813,791 B1 | 10/2010 | Gill et al. |
| 7,881,787 B1 | 2/2011 | Min |

(Continued)

*Primary Examiner* — Michael Kahelin
*Assistant Examiner* — Mitchell E Alter

(57) ABSTRACT

Techniques are provided for use by an implantable medical device or diagnostic sensor for detecting and discriminating euvolemia, hypervolemia and hypovolemia. In one example, the device detects a pressure signal within the patient representative of changes in cardiac pressure overall several cardiac cycles. The device generates separate time-domain and frequency-domain representations of the pressure signal and then discriminates among euvolemia, hypervolemia and hypovolemia within the patient based on an analysis of the time-domain and the frequency-domain representations of the signal. Depending upon the capabilities of the device, suitable warnings may be generated to alert the patient or caregiver. Diuretics or other medications can be titrated to address abnormal fluid conditions such as a fluid overload during hypervolemia. Techniques for detecting a pressure alternans pattern indicative of imminent decompensation are also described.

15 Claims, 14 Drawing Sheets

(56) References Cited

U.S. PATENT DOCUMENTS

| | | |
|---|---|---|
| 7,912,544 B1 | 3/2011 | Min et al. |
| 7,946,995 B1 | 5/2011 | Koh et al. |
| 8,019,409 B2 | 9/2011 | Rosenberg et al. |
| 8,032,212 B2 | 10/2011 | Bornzin et al. |
| 8,202,224 B2 | 6/2012 | Gutfinger et al. |
| 8,452,389 B2 | 5/2013 | Min |
| 8,473,054 B2 | 6/2013 | Pillai et al. |
| 8,473,055 B2 | 6/2013 | Ryu et al. |
| 8,504,153 B2 | 8/2013 | Wenzel et al. |
| 8,527,049 B2 | 9/2013 | Koh et al. |
| 2003/0055345 A1 | 3/2003 | Eigler et al. |
| 2004/0059220 A1* | 3/2004 | Mourad et al. ............. 600/442 |
| 2004/0147969 A1 | 7/2004 | Mann et al. |
| 2004/0167580 A1 | 8/2004 | Mann et al. |
| 2006/0009810 A1 | 1/2006 | Mann et al. |
| 2006/0287602 A1 | 12/2006 | O—Brien et al. |
| 2007/0065363 A1 | 3/2007 | Dalal et al. |
| 2008/0262361 A1 | 10/2008 | Gutfinger et al. |
| 2008/0288030 A1 | 11/2008 | Zhang et al. |
| 2008/0294209 A1 | 11/2008 | Thompson et al. |
| 2008/0306567 A1 | 12/2008 | Park et al. |
| 2009/0270746 A1 | 10/2009 | Min |
| 2009/0287267 A1 | 11/2009 | Wenzel et al. |
| 2010/0069778 A1* | 3/2010 | Bornzin et al. ............. 600/547 |
| 2010/0081942 A1* | 4/2010 | Huiku ............. 600/483 |
| 2010/0152801 A1 | 6/2010 | Koh et al. |
| 2010/0191128 A1* | 7/2010 | Shelley et al. ............. 600/484 |
| 2010/0305641 A1 | 12/2010 | Pillai et al. |
| 2011/0196442 A1 | 8/2011 | Ryu et al. |
| 2011/0213260 A1 | 9/2011 | Keel et al. |

* cited by examiner

SYSTEM AND METHOD FOR DISCRIMINATING HYPERVOLEMIA, HYPERVOLEMIA AND EUVOLEMIA USING AN IMPLANTABLE MEDICAL DEVICE

FIELD OF THE INVENTION

The invention generally relates to implantable medical devices, such as diagnostic sensors, pacemakers, implantable cardioverter/defibrillators (ICDs), and cardiac resynchronization therapy devices (CRTs) (or any combination of these) and in particular to techniques for monitoring blood fluid levels within patients using such devices to detect, distinguish and alert to clinical states of hypervolemia, hypovolemia and euvolemia.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. Progression of HF could lead to congestion wherein the weak pumping of the heart leads to build-up of fluids in the lungs and other organs and tissues.

Pulmonary edema is a swelling and/or fluid accumulation in the lungs often caused by heart failure. Briefly, the poor cardiac function resulting from heart failure can cause blood to back up in the lungs, thereby increasing blood pressure in the lungs, particularly pulmonary venous pressure. The increased pressure pushes fluid—but not blood cells—out of the blood vessels and into lung tissue and air sacs (i.e. the alveoli). This can cause severe respiratory problems and, left untreated, can be fatal. Pulmonary edema can also arise due to other factors besides heart failure, such as infections.

Pulmonary edema due to heart failure may be referred to as cardiogenic pulmonary edema. Significant increase in thoracic fluids is referred to as a "fluid overload." Fluid overload can exacerbate the symptoms of HF and lead to acutely decompensated heart failure, which is a serious and potentially fatal condition. Accordingly, it is highly desirable to detect fluid overload states so that the patient or caregiver can be warned and appropriate therapies delivered. With a fluid overload state, the patient typically becomes hypervolemic (wherein hypervolemia is broadly defined herein as an abnormal increase or shift in blood or fluid volume.) Hence, it would be desirable to equip implantable devices such as diagnostic sensors, pacemakers and CRTs to detect and respond to hypervolemia as an indicator of fluid overload.

One technique for use by an implantable medical device for detecting a fluid overload uses cardiac pressure measurements such as left atrial pressure (LAP) measurements. A significant increase in LAP is deemed to be indicative of such fluid overload. Other pressure parameters that can be used are left ventricular pressure (LVP) and pulmonary artery pressure (PAP.) In response to detection of fluid overload, diuretics can be administered to the patient to reduce the amount of thoracic fluids. Delivery of too large a dosage of diuretics may cause the patient to instead become hypovolemic (wherein hypovolemia is broadly defined herein as an abnormal decrease in blood or fluid volume.) Hypovolemia may arise for other reasons as well. Hence it would also be desirable to equip implantable medical devices to detect and respond to hypovolemia. Ideally, it would be desirable for the device to reliably distinguish or discriminate among hypervolemia, hypovolemia and the healthy volemic state therebetween. The volemic state between hypervolemia and hypovolemia is generally referred to herein as euvolemia (i.e. a normal or healthy volemic state.) Other terms such as optivolemia (i.e. an optimal volemic state) or normovolemia (i.e. a normal volemic state) may also be used herein.

Accordingly, aspects of the invention are generally directed to providing techniques for detecting and discriminating hypervolemia, hypovolemia and euvolemia. Other aspects are directed to detecting other conditions or states, such as a pressure alternans state indicative of imminent heart failure decompensation.

SUMMARY OF THE INVENTION

In accordance with an exemplary embodiment of the invention, techniques are provided for use by an implantable medical device for detecting and discriminating euvolemia, hypervolemia and hypovolemia. In one example, the device detects a pressure signal within the patient representative of changes in cardiac pressure during at least one cardiac cycle. The device generates separate time-domain and frequency-domain representations of the pressure signal and then discriminating among euvolemia, hypervolemia and hypovolemia within the patient based on the separate time-domain and the frequency-domain characteristics of the pressure signal. Depending upon the capabilities of the device, suitable warnings may be generated to alert the patient or caregiver. Diuretics or other medications can be titrated to address abnormal fluid conditions such as a fluid overload during hypervolemia.

In an illustrative embodiment, the device is a standalone diagnostic device or a pacemaker, ICD or CRT in combination with implantable diagnostic sensors to detect time-varying pressure signals representative of one or more of LVP, LAP or PAP. A fast Fourier transform (FFT) is used to generate a frequency-domain representation of the time-varying pressure signals for analysis along with the time-domain pressure signal. The frequency-domain signals are analyzed to assess the distribution of signal power and, in particular, to determine whether power is narrowly concentrated at power spectra peaks associated with the heart rate and its harmonics rather than diffused among wider frequencies. The time-domain signals are analyzed to identify the ejection period of the cardiac cycle and to assess the shape of the signals during the ejection period. The shape may be relatively sharply peaked or it might instead be relatively rounded. To assess the shape of the pressure signal within the ejection period, the device generates a shape index or metric based on a best-fit quadratic curve or a best-fit cosine curve for comparison against a programmable threshold set to distinguish a peaked shape from a non-peaked (i.e. more rounded) shape. The device then discriminates euvolemia, hypervolemia and hypovolemia based on these parameters. Hypervolemia is indicated if the shape of the pressure signal during the ejection period is relatively sharply peaked and the signal power is concentrated at the power spectra peaks associated with heart rate and its harmonics. Hypovolemia is indicated if the signal power is concentrated but the shape of pressure signal during the ejection period is a relatively more rounded rather than sharply peaked. Euvolemia is instead indicated if the pressure signal during the ejection period is a relatively rounded but the signal power is diffused among wider frequency bands rather than concentrated. Table I illustrates these parameters.

TABLE I

| VOLUME STATE | TIME DOMAIN CHARACTERISTICS | FREQUENCY DOMAIN CHARACTERISTICS |
|---|---|---|
| Hypervolemic | Peaked pressure signal during ejection period | Signal power concentrated at heart rate and its harmonics |
| Hypovolemic | Rounded pressure signal during ejection period | Signal power concentrated at heart rate and its harmonics |
| Euvolemic | Rounded pressure signal during ejection period | Signal power diffused over wider range of frequencies |

In some examples, additional or alternative parameters are used to in the discrimination procedure. For instance, the device can detect the time of the peak of the pressure signal within the cardiac cycle (P max) and determine whether it occurs relatively early or relatively late within a window defined by dP/dt max and dP/dt min. An early time of P max is indicative of hypervolemia. A later time is consistent with a lack of hypervolemia. Accordingly, an index or metric may be generated that is representative of the location of P max within said window for comparison against a threshold set to detect an early P max due to possible hypervolemia. As another example, the device can assess the frequency and width of the first peak of the frequency-domain representation of the pressure signal (which is associated with heart rate.) During hypervolemia, the center frequency of the first peak tends to increase while the width tends to decrease due to an imbalance in sympathetic tone. Accordingly, both the frequency and width of the spectral peak associated with heart rate can be assessed to detect or corroborate hypervolemia. Additionally, the ratio of the magnitude of the first harmonic to the magnitude of zeroth harmonic (i.e. the heart rate peak) can be assessed to detect a possible pressure alternans pattern indicative of imminent heart failure decompensation. If the ratio is high (i.e. the first harmonic is as large as or larger than the zeroth harmonic), pressure alternans is indicated and urgent warnings are generated. The power of various harmonics can additionally or alternatively be assessed as a separate metric for discrimination purposes.

In examples where the device examines pressure signals during the ejection period, the location of the ejection period within the cardiac cycle is detected or estimated based on fiducial markers identified within the time-varying pressure signal. In one example, the device determines first order derivatives (dP/dt) and second order derivatives ($d^2P/dt^2$) of the pressure signal within the cardiac cycle. The device identifies fiducial markers based on the first and second order derivatives including: a maximum magnitude of dP/dt (dP/dt max); a time of dP/dt max; a minimum magnitude of dP/dt (dP/dt min); a time of dP/dt min; a peak magnitude of the pressure (P max); a time of P max; a minimum magnitude of $d^2P/dt^2$ and a maximum magnitude of $d^2P/dt^2$. The device then identifies the ejection period as the interval between the time of minimum $d^2P/dt^2$ after dP/dt max and the time of minimum $d^2P/dt^2$ before dP/dt min (which corresponds to the interval between the opening and closing of the semilunar valves of the heart of the patient.)

In some examples, rather than discriminating among euvolemia, hypervolemia and hypovolemia, the device instead discriminates between a hypervolemic state and a non-hypervolemic state. This may be achieved based on an examination of the time-varying pressure signal without necessarily generating or examining the frequency-domain representation of the pressure signal. In one example, the device assesses the shape of the pressure signal during the ejection period and then associates a peaked shape with hypervolemia and a non-peaked shape with a lack of hypervolemia (i.e. hypovolemia or euvolemia.) Alternatively, the device can discriminate between a euvolemic state and a non-euvolemic state (i.e. an abnormal state) based on an examination of the frequency-domain representation of the pressure signals. In one example, the device assesses whether signal power is relatively concentrated at the frequencies of the heart rate and its harmonics rather than diffused among wider frequencies. A more diffused power spectrum is associated with euvolemia (i.e. a normal volemic state.) A narrow concentration of power at higher frequencies of heart rate and its harmonics is associated with a non-euvolemic or abnormal state (i.e. hypervolemia or hypovolemia.)

In some implementations, a drug pump is implanted within the patient to directly provide suitable diuretics in response to detection of hypervolemia associated with a fluid overload. The implanted device (IMD) directly controls the delivery and titration of the diuretics in response to the fluid overload. In other implementations, the IMD transmits information to an external device (such as a bedside monitor or hand-held interface device) for notifying the patient or caregiver of the need to adjust the dosage of diuretics or other medications.

System and method examples of these techniques are described herein.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
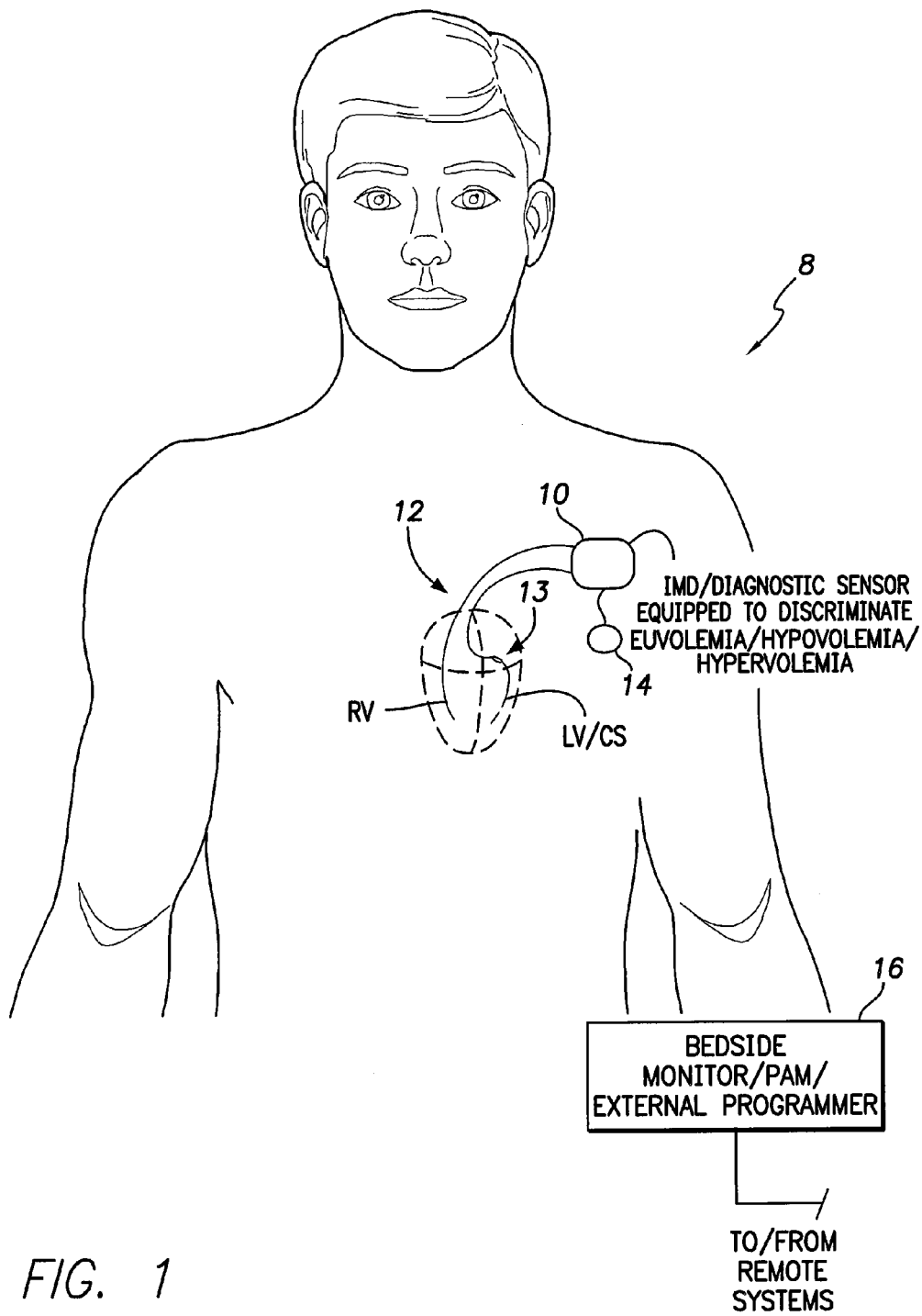
FIG. 1 illustrates pertinent components of an implantable medical system having an IMD and/or stand-alone diagnostic sensor capable of detecting and discriminating hypervolemia, hypovolemia and euvolemia.
Figure 13:
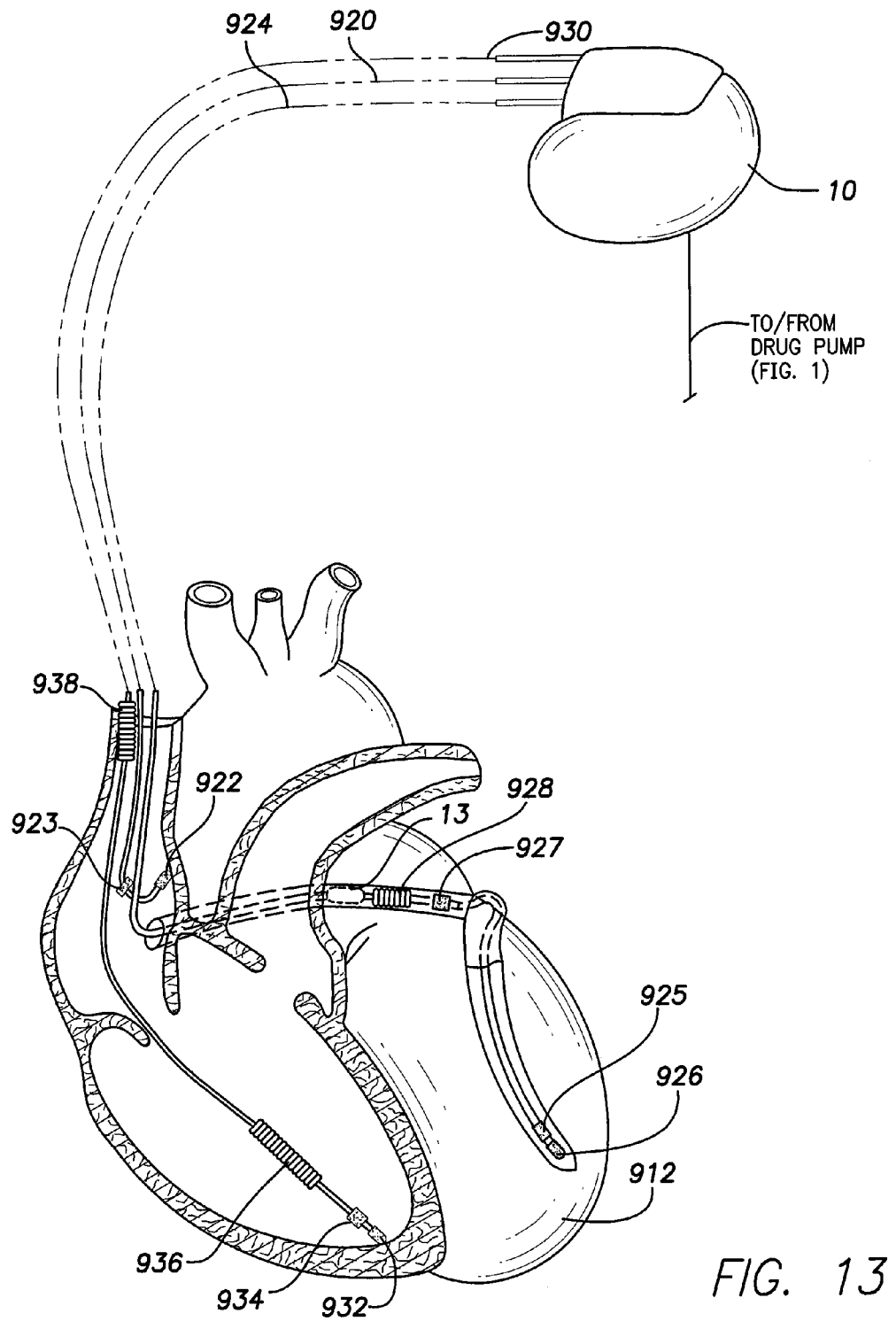
FIG. 13 is a simplified, partly cutaway view, illustrating the device of FIG. 1 along with a set of leads implanted into the heart of the patient.

FIG. 1 illustrates an implantable medical system 8 capable of detecting and discriminating hypervolemia, hypovolemia and euvolemia based on time-varying pressure LAP measurements (or other pressure measurements such as LVP or PAP) made during individual cardiac cycles. The system is further capable of titrating dosages of diuretics or other medications in response, as well as performing various other therapeutic or diagnostic functions. To these ends, medical system 8 includes a diagnostic sensor and/or IMD 10 or other cardiac rhythm management device equipped with one or more cardiac sensing/pacing leads 12 implanted within the heart of the patient. In FIG. 1, only two exemplary leads are shown: an RV lead and an LV lead implanted via the coronary sinus (CS). A more complete set of leads is illustrated in FIG. 13. Although identified as an "IMD/diagnostic sensor" in FIG. 1, it should be understood that device 10 can be any suitably-equipped implantable medical device, diagnostic sensor or other system/device/apparatus, such as a standalone implantable sensor device or pacemaker, ICD or CRT device, including CRT-D and CRT-P devices. In the following, for brevity, device 10 will be referred to simply as an IMD.

An exemplary LAP transducer sensor 13 is shown mounted to the LV/CS lead on or near the left atrium for sensing LAP. This particular LAP sensing configuration is merely illustrative. More information regarding LAP sensors and suitable locations for mounting such sensors are discussed in, for example, U.S. Patent Application 2003/0055345 of Eigler et al., entitled "Permanently Implantable System and Method for Detecting, Diagnosing and Treating Congestive Heart Failure," now U.S. Pat. No. 7,137,953. See, also, U.S. patent application Ser. No. 11/856,443, filed Sep. 17, 2007, of Zhao et al., entitled "MEMS-Based Left Atrial Pressure Sensor for use with an Implantable Medical Device," now abandoned. Other sensors such as LVP or PAP sensors are discussed below.

In examples where the system is intended to automatically titrate diuretics based on the volemic state, an implanted or subcutaneous drug pump or other drug dispensing device 14 may be used, which is controlled by the IMD. Implantable drug pumps for use in dispensing medications are discussed in U.S. Pat. No. 5,328,460 to Lord, et al., entitled "Implantable Medication Infusion Pump Including Self-Contained Acoustic Fault Detection Apparatus."

In other embodiments, information pertaining to the volemic state is transmitted to an external system 16, which generates diagnostic displays instructing the patient to take certain dosages of diuretics or other medications. System 16 may include, for example, an external programmer, bedside monitor or hand-held personal advisory module (PAM). Data from the external system can be forwarded to a centralized system such as the Merlin.Net system, through the HouseCall™ remote monitoring system or the Merlin@home systems of St. Jude Medical for notifying the clinician of hypervolemia, hypovolemia or other abnormal conditions detected by the device.

Warnings pertaining to hypervolemia or hypovolemia may also be generated using the bedside monitor, PAM/mobile patient interface, or an internal warning device provided within the IMD. The internal warning device (which may be part of IMD) can be a vibrating device or a "tickle" voltage device that, in either case, provides perceptible stimulation to the patient to alert the patient. (Again, see Lord et al.) The bedside monitor or PAM can provide audible or visual alarm signals to alert the patient or caregiver, as well as any appropriate textual or graphic displays. In addition, diagnostic information pertaining to changes in fluid levels (and pertaining to any medical conditions detected therefrom) may be stored within the IMD for subsequent transmission to an external programmer for review by a clinician during a follow-up session between patient and clinician. The clinician then prescribes appropriate therapies to address the condition. The clinician may also adjust the operation of the IMD to activate, deactivate or otherwise control any therapies provided.

Additionally, the IMD performs a wide variety of pacing and/or defibrillation functions such as delivering pacing in response to an arrhythmia or generating and delivering shocks in response to fibrillation. Also, in some examples, the device delivers CRT. Briefly, CRT seeks to normalize asynchronous cardiac electrical activation and resultant asynchronous contractions associated with HF by delivering synchronized pacing stimulus to both ventricles. The stimulus is synchronized so as to improve overall cardiac function. This may have the additional beneficial effect of reducing the susceptibility to life-threatening tachyarrhythmias. CRT is discussed in: U.S. Pat. No. 8,019,409 to Rosenberg et al., entitled "Cardiac Resynchronization Therapy Optimization using Electromechanical Delay from Realtime Electrode Motion Tracking"; U.S. Patent Application No. 2011/0213260 of Keel et al., entitled "CRT Lead Placement based on Optimal Branch Selection and Optimal Site Selection," now abandoned; U.S. Patent Application No. 2011/0196442 of Ryu et al., entitled "Systems and Methods for Optimizing Multi-Site Cardiac Pacing and Sensing Configurations for use with an Implantable Medical Device," now U.S. Pat. No. 8,473,055; and U.S. Patent Application No. 2010/0152801 of Koh et al., entitled "Cardiac Resynchronization Therapy Optimization Using Vector Measurements Obtained from Realtime Electrode Position Tracking," now U.S. Pat. No. 8,527,049. See, also: U.S. Patent Application No. 2008/0306567 of Park et al., entitled "System and Method for Improving CRT Response and Identifying Potential Non-Responders to CRT Therapy," now U.S. Pat. No. 8,301,246; U.S. Pat. No. 7,912,544 to Min et al., entitled "CRT Responder Model using EGM Information"; and U.S. Pat. No. 7,881,787 to Min, entitled "Capture Detection System and Method CRT Therapy."

Note that systems provided in accordance with the invention need not include all the components shown in FIG. 1. In many cases, for example, the implantable system will include only the IMD and its leads. Drug pumps are not necessarily employed. Some implementations may employ an external monitor for generating warning signals but no internal warning device. These are just a few exemplary embodiments. No attempt is made herein to describe all possible combinations of components that may be provided in accordance with the general principles of the invention. Also, note that, although internal signal transmission lines are shown in FIG. 1 for interconnecting implanted components, wireless signal transmission might alternatively be employed. In addition, it should be understood that the particular shape, size and locations of the implanted components shown in FIG. 1 are merely illustrative and may not necessarily correspond to actual implant locations. In particular, preferred implant locations for the leads are more precisely illustrated in FIG. 13.

Hypervolemia/Hypovolemia/Euvolemia Detection and Discrimination Techniques

Figure 2:
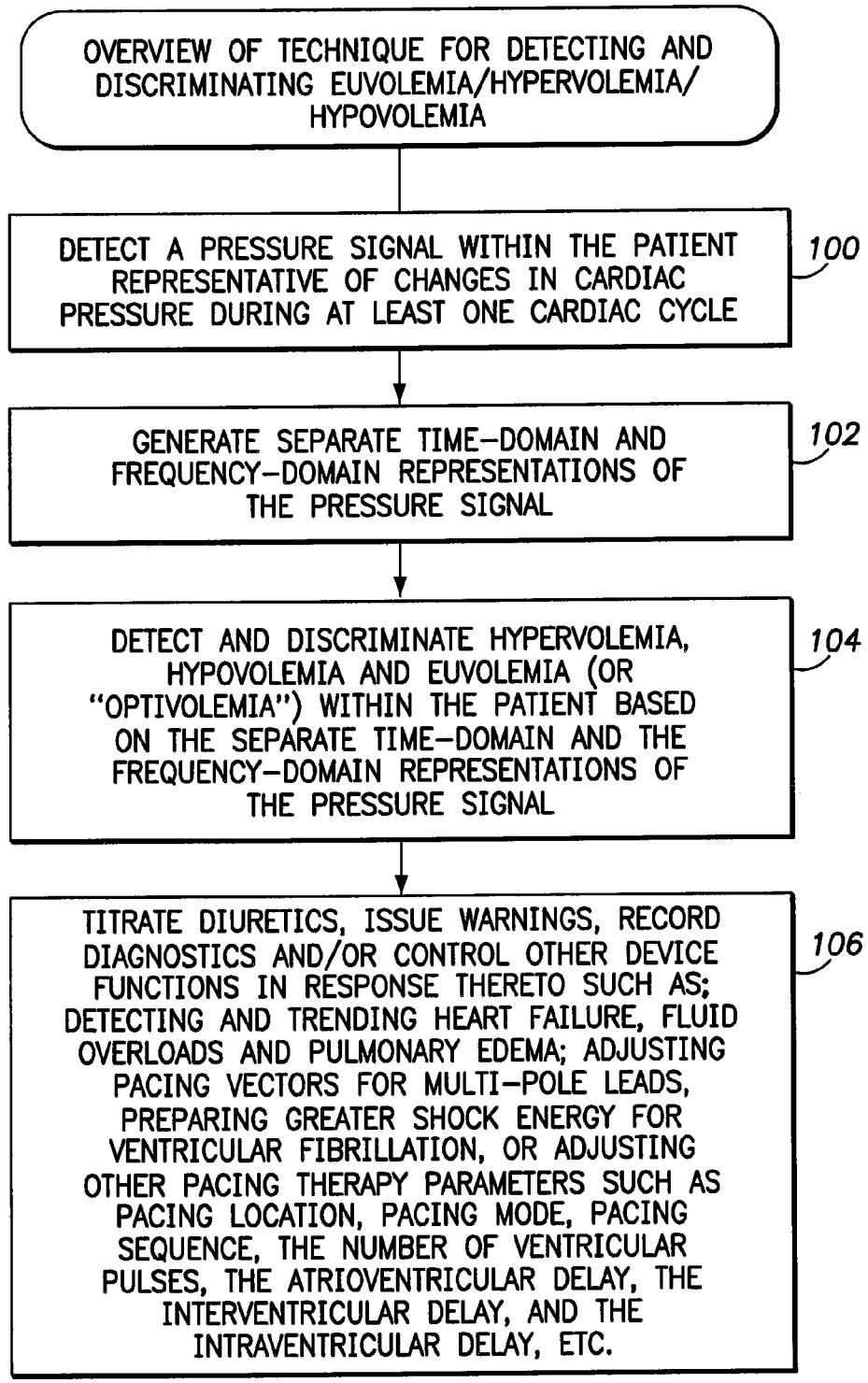
FIG. 2 summarizes techniques for detecting and discriminating hypervolemia, hypovolemia and euvolemia performed by the system of FIG. 1.

FIG. 2 broadly summarizes a general technique for detecting and discriminating hypervolemia, hypovolemia and euvolemia based on pressure measurements made during cardiac cycles. At step 100, the IMD detects a pressure signal within the patient representative of changes in cardiac pressure during at least one cardiac cycle. Typically, this is a time-varying pressure signal that varies in response to pressure changes in the ventricles of the heart during cardiac cycles. The pressure signal may be, for example, LAP, LVP or PAP. LAP sensors are discussed above. LVP sensors are discussed, for example, in U.S. Pat. No. 6,666,826 to Salo, et al., entitled "Method and apparatus for measuring left ventricular pressure." For PAP sensors, see, for example, U.S. Pat. No. 7,195,594 to Eigler, et al., entitled "Method for Minimally Invasive Calibration of Implanted Pressure Transducers" and U.S. Pat. No. 7,621,879 also of Eigler, et al., entitled "System for Calibrating Implanted Sensors." Sensors for use in the pulmonary artery are also discussed, for example, in U.S. Pat. No. 7,621,036 of Cros et al., entitled "Method of Manufacturing Implantable Wireless Sensor for In Vivo Pressure Measurement" and in U.S. Patent Application 2006/0287602 of O'Brien et al., entitled "Implantable Wireless Sensor for In Vivo Pressure Measurement." See, also, U.S. Pat. No. 7,460,909 of Koh, et al., entitled "Implantable Device for Monitoring Hemodynamic Profiles." It may also be appropriate in some implementations to estimate LAP, LVP or PAP based on impedance signals or other proxies or surrogates so long as the approximation is a suitable waveform. See, for example: U.S. Pat. No. 7,794,404 to Gutfinger et al., entitled "System and Method for Estimating Cardiac Pressure using Parameters Derived from Impedance Signals detected by an Implantable Medical Device"; U.S. Patent Application 2009/0287267 of Wenzel et al., "System and Method for Estimating Cardiac Pressure Based on Cardiac Electrical Conduction Delays Using an Implantable Medical Device," now U.S. Pat. No. 8,504,153; and U.S. Patent Application 2008/0262361 of Gutfinger et al., entitled "System and Method for Calibrating Cardiac Pressure Measurements Derived from Signals Detected by an Implantable Medical Device," now U.S. Pat. No. 8,202,224.

At step 102, the device generates separate time-domain and frequency-domain representations of the pressure signal by, for example, applying an FFT to an initial time-varying pressure signal to generate a frequency-domain or spectral version of the signal. Note that no processing is necessary to generate a time-domain representation of the pressure signal if the initial input signal is a time-varying pressure signal (and hence already in the time-domain.) However, in at least some embodiments, some processing might be employed to filter the time-varying signal to eliminate noise or the like. Also, in rare cases, if the initial input pressure signal were instead a frequency-domain signal, then conversion to time-domain might be needed.

At step 104, the device detects and/or discriminates hypervolemia, hypovolemia and euvolemia (or "optivolemia") within the patient based on the separate time-domain and frequency-domain representations of the pressure signal using techniques to be described in greater detail below. Note that the term optivolemia is intended herein to be synonymous with euvolemia. That is, the device does not seek to identify a truly optimal volemic state for the patient as a truly optimal state might be difficult to characterize or define. Rather, the device seeks to distinguish a generally healthy or normal volemic state from abnormal states. At step 106, in response thereto, the device titrates diuretics, issues warnings pertaining to hypervolemia or hypovolemia, records diagnostics and/or controls other device functions. The other device functions to be controlled can comprise any function that can be performed or controlled by the device (alone or in combination with other devices) such as detecting or trending heart failure, pulmonary edema, fluid overloads, decompensation or other medical conditions based in whole or in part on the indication of hypervolemia or hypovolemia. Other functions to be controlled can include adjusting pacing vectors for multi-pole leads or preparing greater shock energy for ventricular fibrillation based on the assessment or adjusting pacing therapy parameters including but not limited to pacing location, pacing mode, pacing sequence, number of ventricular pulses, atrioventricular delay, interventricular delay, and intraventricular delay. In this regard, if the assessment indicates significant hypervolemia (associated with heart failure), the device can adjust or change the pacing vectors in response to such heart failure (assuming it is so equipped.) Since heart failure can result in a greater likelihood of ventricular fibrillation (VF) and the need for a defibrillation shock, the device can pre-charge shock capacitors or take other appropriate steps in expectation of possible delivery of a shock, particularly if VF is deemed imminent. Insofar as titration of therapy is concerned, decongestive therapy titration is discussed in: U.S. Patent Application 2008/0294209 of Thompson et al., entitled "Decongestive Therapy Titration for Heart Failure Patients using Implantable Sensor."

Figure 3:
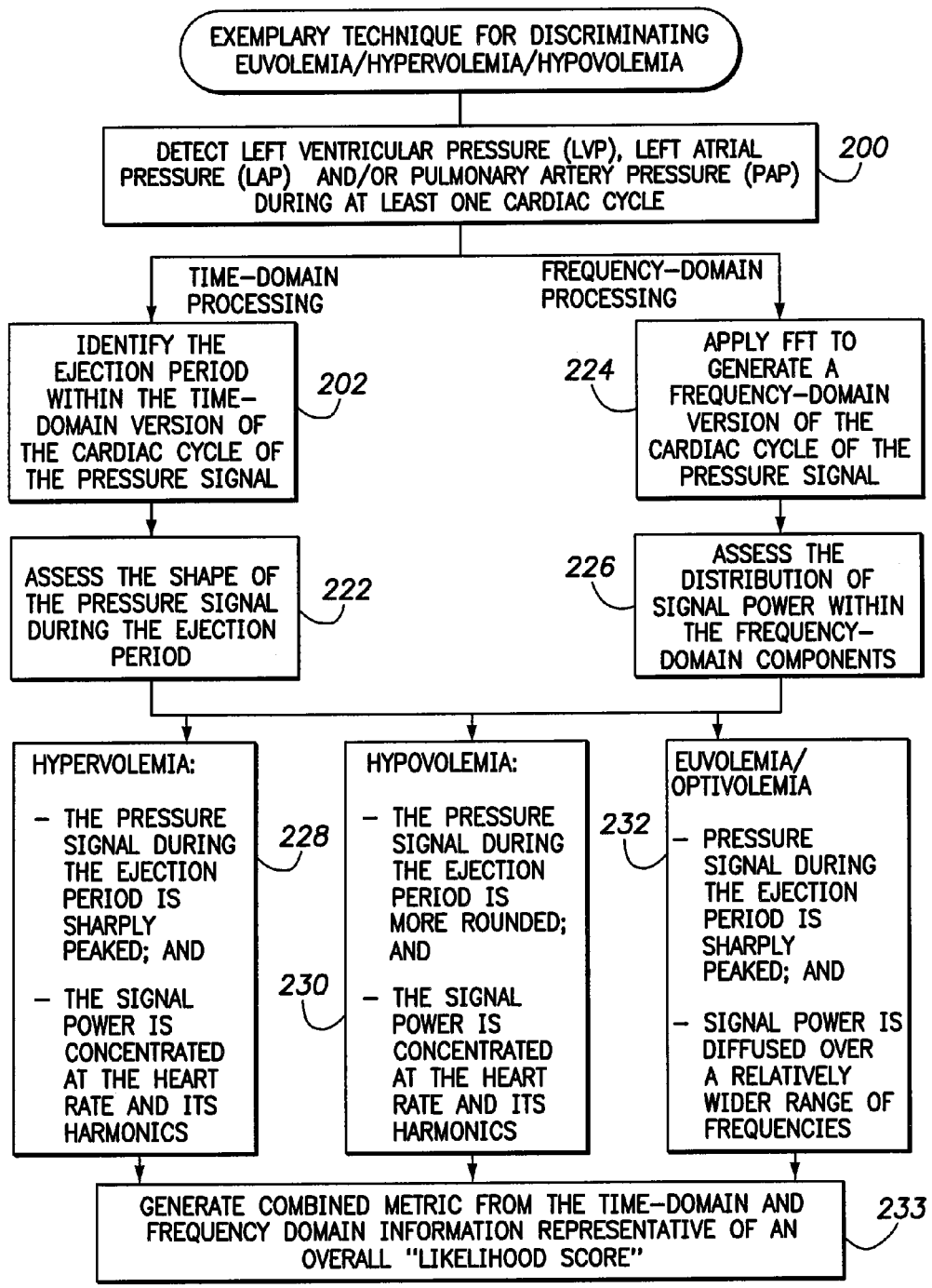
FIG. 3 illustrates an exemplary embodiment of the detection and discrimination technique of FIG. 2 that highlights the separate time-domain and frequency domain processing.

FIG. 3 illustrates an exemplary embodiment of the general method of FIG. 2 that highlights the separate time-domain and frequency-domain processing. At step 200, the IMD detects LVP, LAP, or PAP during at least one cardiac cycle as already discussed. The values obtained over multiple cardiac cycles can be averaged where appropriate. Preferably, pressure tracings obtained over at least fifteen seconds are obtained before processing commences. At step 202, as part of the time-domain processing, the device identifies or estimates the ejection period or ejection interval within the time-domain representation of the pressure signal. The ejection period is the second phase of ventricular systole, i.e. the interval between the opening and closing of the semilunar valves during which blood is discharged from the ventricles into the aortic and pulmonary arteries. Exemplary techniques for identifying or estimating the location of the ejection period within the cardiac cycle based on fiducial markers are discussed in greater detail below.

Figure 4:
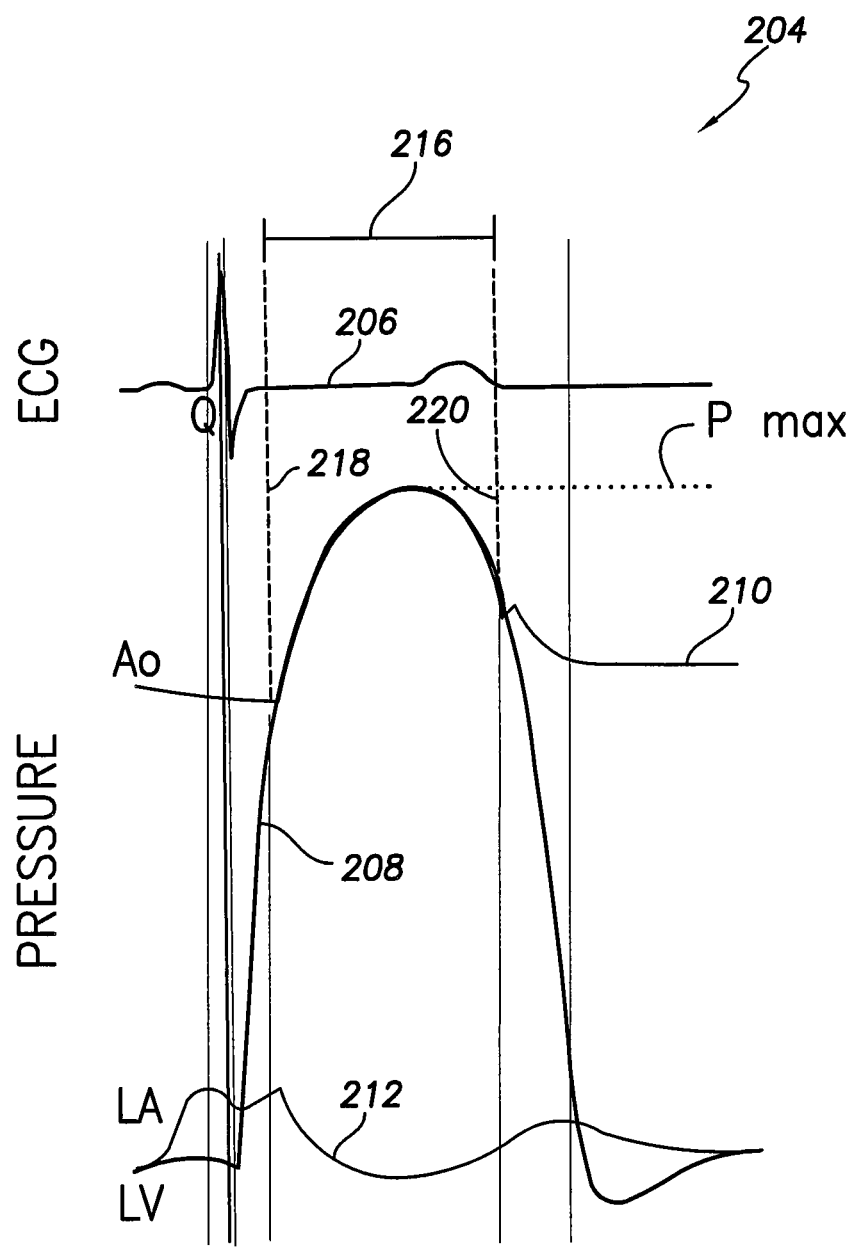
FIG. 4 is a graph illustrating exemplary variations in ventricular pressure during a cardiac cycle exploited by the technique of FIG. 3.

FIG. 4 illustrates a portion 204 of an exemplary cardiac cycle by way of an electrocardiogram (ECG) trace 206, a ventricular pressure trace 208, an aortic pressure trace 210 and an atrial pressure trace 212. The ejection period 216 begins at time 218 corresponding to the opening of the aortic and pulmonary valves and ends at time 220 corresponding to the closing of the aortic and pulmonary valves. During this interval of time, ventricular pressure initially increases before reaching a peak (P max) and then decreases. Both the shape and location of the peak may be exploited to aid in the discrimination procedure.

Figure 8:
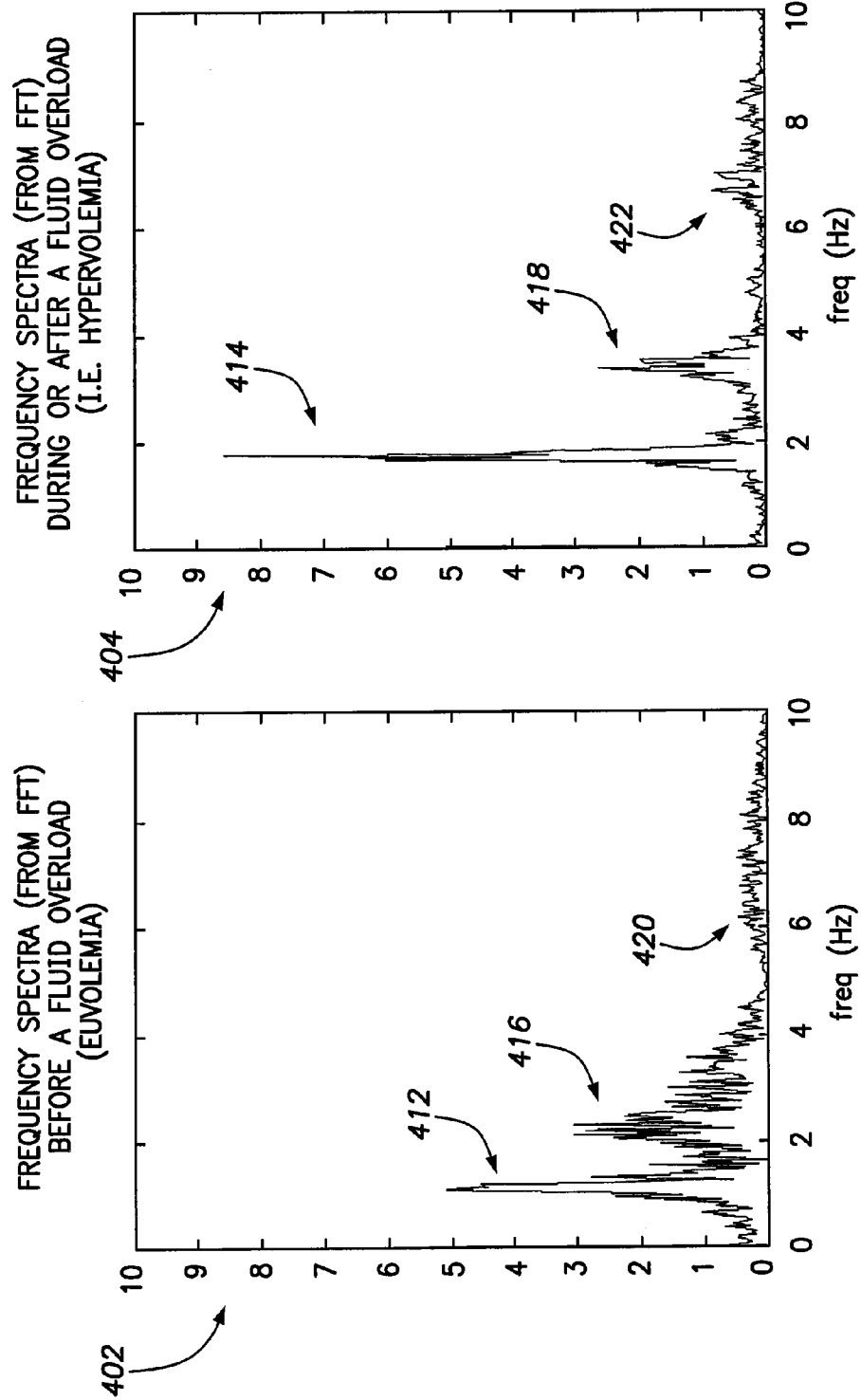
FIG. 8 is a graph of FFT spectra illustrating exemplary shape and frequency differences in pressure signals exploited by the technique of FIG. 5 to distinguish hypervolemia due to a fluid overload from euvolemia or hypovolemia.

Returning to FIG. 3, the IMD at step 222 assesses the shape of the pressure signal during the ejection period to determine whether it is sharply peaked or more rounded. (Analysis of the relative location of P max is discussed below with reference to the more detailed time-domain processing example of FIG. 5.) Meanwhile, at step 224, the device applies an FFT to generate a frequency-domain representation of the cardiac cycle of the pressure signal. An example of a frequency-domain representation of a pressure signal is shown in FIG. 8, discussed below. FFTs are discussed in U.S. Pat. No. 7,813,791 to Gill et al., entitled "Systems and Methods for Employing an FFT to Distinguish R-waves from T-waves using an Implantable Medical Device." At step 226, the device assesses the distribution of signal power within the frequency-domain representation of the pressure signal, particularly to ascertain whether power is concentrated near the frequencies of the heart rate and its harmonics or is more widely distributed or diffused among a wider range of frequencies.

Following steps 222 and 226, the device has thereby ascertained the shape of the time-domain pressure signal within the ejection period and the distribution of power with the frequency-domain representation. Based on this information, the device discriminates hypervolemia, hypovolemia and euvolemia in accordance with the general conditions set forth in Table I above. At step 228, hypervolemia is indicated if (a) the pressure signal during the ejection period is sharply peaked and (b) the signal power is concentrated at the heart rate and its harmonics. At step 230, hypovolemia is indicated if (a) the pressure signal during the ejection period is relatively more rounded and (b) the signal power is concentrated at the heart rate and its harmonics. At step 232, euvolemia or optivolemia is indicated if (a) the pressure signal during the ejection period is sharply peaked and (b) the signal power is diffused over a relatively wider range of frequencies. At step 233, the device can also generate a combined metric from the time-domain and frequency domain information representative of an overall likelihood score, i.e. a numerical value representative of the likelihood of being hyper-/hypo-/euvolemic. For example, referring to Table I, the device can assign a score of "1" for criteria that match "Peaked pressure signal during ejection period," a score of "1" for all criteria that match "Signal power concentrated at heart rate and its harmonics," and "0" for the opposing cases. Then, based on Table I, the device generates a total score of "2," "1," and "0" for hypervolemic, hypovolemic, euvolemic, respectively. A threshold can be set against this overall "likelihood score" to aid in discriminating the volemic state of the patient for triggering therapy, etc.

Figure 5:
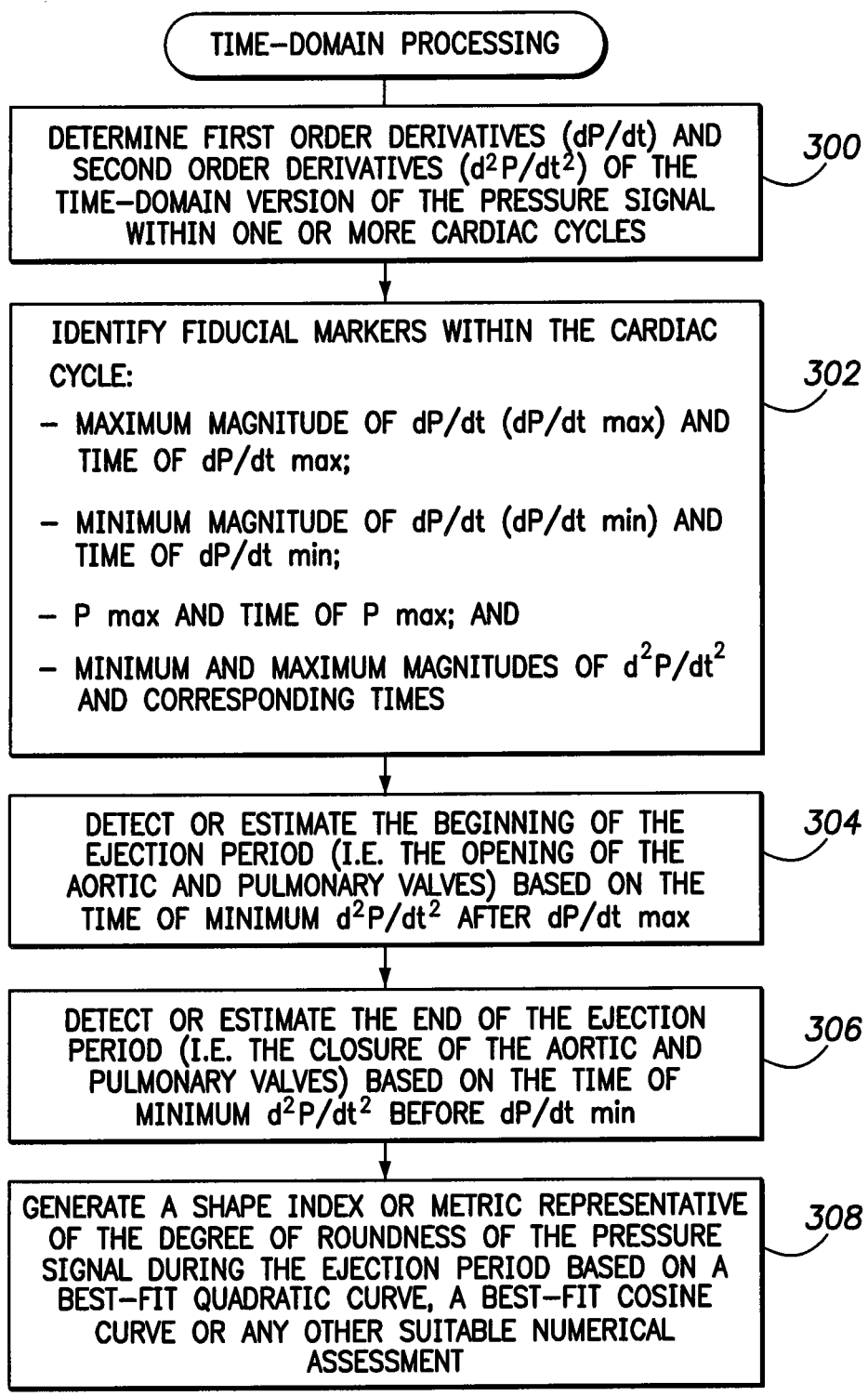
FIG. 5 illustrates time-domain processing in greater detail for use with the exemplary detection and discrimination technique of FIG. 3.
Figure 6:
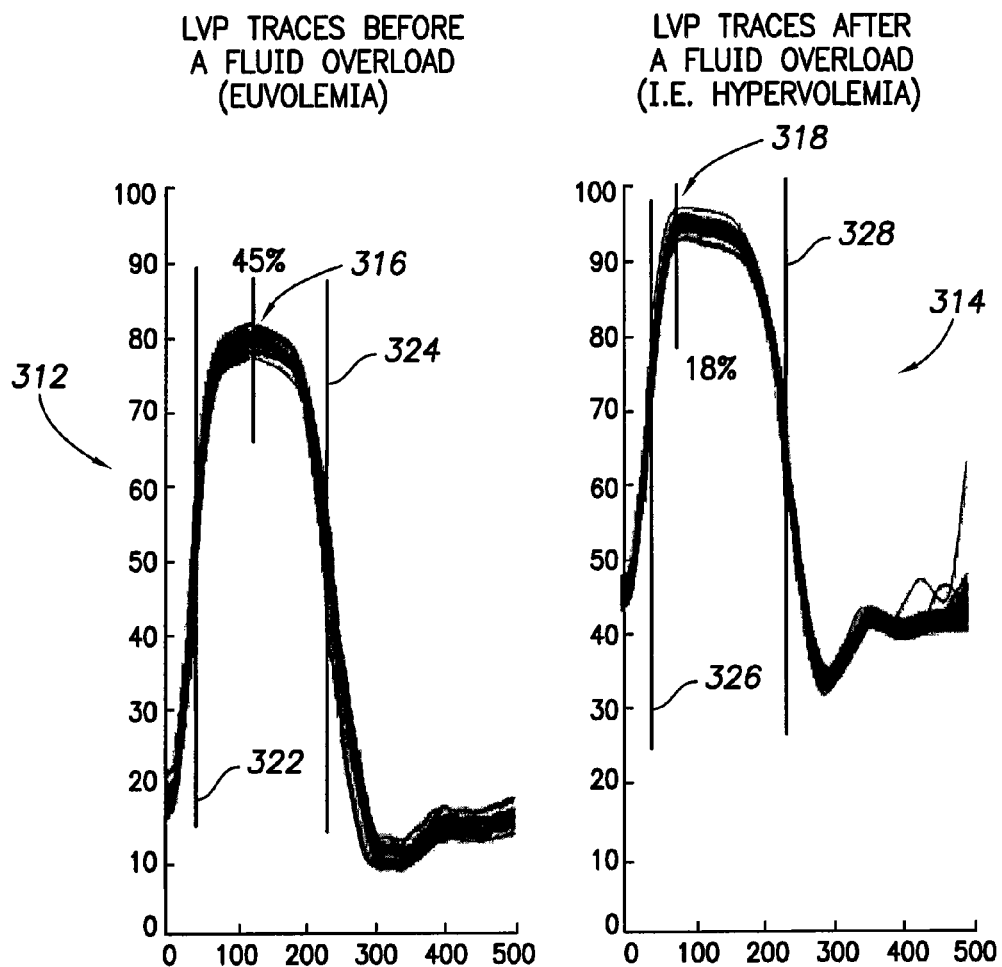
FIG. 6 is a graph of LVP traces illustrating exemplary shape and timing differences in pressure signals within the ejection period exploited by the technique of FIG. 5 to distinguish hypervolemia due to a fluid overload from euvolemia or hypovolemia.

Thereafter, the device responds by controlling therapy, generating warnings, etc., as already discussed. Turning next to FIGS. 5 and 6, time-domain processing of pressure signals will be described in greater detail.

FIG. 5 illustrates an exemplary time-domain processing technique for used in detecting and discriminating hypervolemia from hypovolemia and euvolemia. At step 300, the IMD determines first order derivatives (dP/dt) and second order derivatives ($d^2P/dt^2$) of the time-domain representation of the pressure signal within one or more cardiac cycles. At step 302, the device identifies various fiducial markers within the cardiac cycle including: the maximum magnitude of dP/dt (dP/dt max); the time of dP/dt max; the minimum magnitude of dP/dt (dP/dt min); the time of dP/dt min; the peak magnitude of the pressure (P max); the time of P max; the minimum magnitude of $d^2P/dt^2$ and its time; and the minimum magnitude of $d^2P/dt^2$ and its time. At step 304, the device detects or estimates the beginning of the ejection period (i.e. the opening of the semilunar valves) based on the time of minimum $d^2P/dt^2$ after dP/dt max. (See, time 218 in FIG. 4.) At step 306, the device also detects or estimates the end of the ejection period (i.e. the closure of the semilunar valves) based on the time of minimum $d^2P/dt^2$ before dP/dt min. (See, time 220 in FIG. 4.)

At step 308, the device generates a shape index or metric representative of the degree of roundness in the pressure signal during the ejection period based on best-fit quadratic curve, a best-fit cosine curve or other suitable numerical assessment. That is, the shape index quantifies whether the pressure signal during the ejection period is relatively rounded or instead relatively peaked. One way to accomplish this is for the device to either find the power of the quadratic (square, cubed, or similar) or the coefficient of the cosine function once it is fit. Alternatively, a template cosine or quadratic could be applied to all the pressure waveforms and the cumulative difference from that template (i.e. the error) could be used; that is, the higher the error the more "peaked" it is and the lower the error, the more rounded. In one particular example, the shape index is generated by: identifying and using the order of best-fit quadratic; indentifying and using the coefficient of the best-fit cosine curve; applying a pre-determined quadratic, determining the cumulative difference between the quadratic and the acquired waveform and using this cumulative difference; and then applying a pre-determine cosine curve, determining the cumulative difference between the curve and the acquired waveform and using this cumulative difference.

Note that, although referred to herein as a "shape index," the index could instead be referred to by other terms such as a "smoothness index," a "peak sharpness index" or even a "flatness index." At step 310, the device compares the shape index against a suitable shape index threshold to distinguish a sharply peaked shape from a more rounded shape. A suitable shape index threshold (which is a programmable value) can be determined in advance for a particular patient while the patient is known to be euvolemic. This may be done as part of a post-implant follow-up programming session with the clinician, thereby allowing the clinician to set or adjust the threshold, as needed. The particular threshold value will depend, of course, on the particular technique used to assess or quantify the shape index. The threshold is then programmed into the device. In some examples, the threshold may be specified in terms of a percentage change in the shape index value. For example, a 10% increase in the shape index (indicative of a 10% increase in the sharpness of the pressure signal) would be deemed to indicate possible hypervolemia.

FIG. 6 illustrates the difference between the generally rounded pressure profile associated with euvolemia and the more sharply peaked pressure profile associated with hypervolemia by way of LVP traces during ejection. More specifically, a first graph 312 presents LVP traces during the ejection period for euvolemia (before a fluid overload) whereas a second graph 314 presents LVP traces during the ejection period for hypervolemia (after or during a fluid overload.) In each case, an ensemble of traces is shown corresponding to set of cardiac cycles to illustrate that slight variations from one cycle to another can occur. Preferably, during processing, pressure signals from a set of cardiac cycles are averaged together to improve the robustness and reliability of the time-domain analysis. Comparing the shape of pressure peak 316 of graph 312 with the shape of pressure peak 318 of graph 314, it can be seen that peak 316 is relatively smoother and more rounded than peak 318. Alternatively, peak 318 may be regarded as being more sharply "peaked" than smoother peak 316. As such, a shape index generated from the traces of graph 312 would be indicative of a more rounded shape than the shape index generated from the traces of graph 314. In an example where the value of the shape index increases with increasing peak sharpness, the index generated from the traces of graph 314 would therefore have a higher numerical value than the index generated from the traces of graph 312.

In addition to assessing the shape of the pressure signal during ejection, the device also assesses the location of the peak (P max) of the pressure signal. Accordingly, at step 320 of FIG. 5, the device determines the time of P max relative to a window defined by dP/dt max and dP/dt min. Within graph 312 of FIG. 6, the time of dP/dt max is indicated by line 322. The time of dP/dt min is indicated by line 324. Within graph 314, the time of dP/dt max is indicated by line 326. The time of dP/dt min is indicated by line 328. (Note that the beginning and end points of the ejection period, which can differ somewhat from the dP/dt max and dP/dt min times, are not explicitly marked in FIG. 6. See, FIG. 4 for an illustration of the ejection period, which is instead detected based on the timing of $d^2P/dt^2$ values.)

At step 330 of FIG. 5, the device then generates a P max index or metric indicative of whether the time of P max is closer to dP/dt max or dP/dt min and then compares the index against a P max index threshold. That is, the P max index quantifies whether the peak of the pressure signal occurs relatively early or relatively late within the window defined by the time between dP/dt max or dP/dt min. In one particular example, a P max index of 0% would indicate that the peak occurs at or near dP/dt max (i.e. very early.) A P max index of 100% would indicate that the peak occurs at or near dP/dt min (i.e. very late.) In the example of FIG. 6, the P max index for the euvolemic traces of graph 312 is 45%, indicating that P max occurs about midway between dP/dt max and dP/dt min. The P max index for the hypervolemic traces of graph 314 is 18%, indicating that P max occurs much earlier within the window of interest. (Note that, although referred to herein as a "P max index," the index could instead be referred to by other terms such as a "peak timing index.")

A suitable P max index threshold for use at step 330 of FIG. 5 can be determined in advance for a particular patient while the patient is known to be euvolemic. (As with the shape index threshold, the P max index threshold may be set during a post-implant programming or a remote-monitoring session with the clinician, allowing the clinician to set or adjust the threshold as needed.) The threshold is then programmed into the device. In some examples, the P max threshold may be specified in terms of a percentage value. For example, the threshold might be set to 30% such that if the P max index is less than 30%, hypervolemia is indicated. If the P max index is not less than 30%, hypervolemia is not indicated. The "P max index" can also be used to drive a scoring system that brings both the shape and frequency determination together, and a threshold is created from total score.

Figure 7:
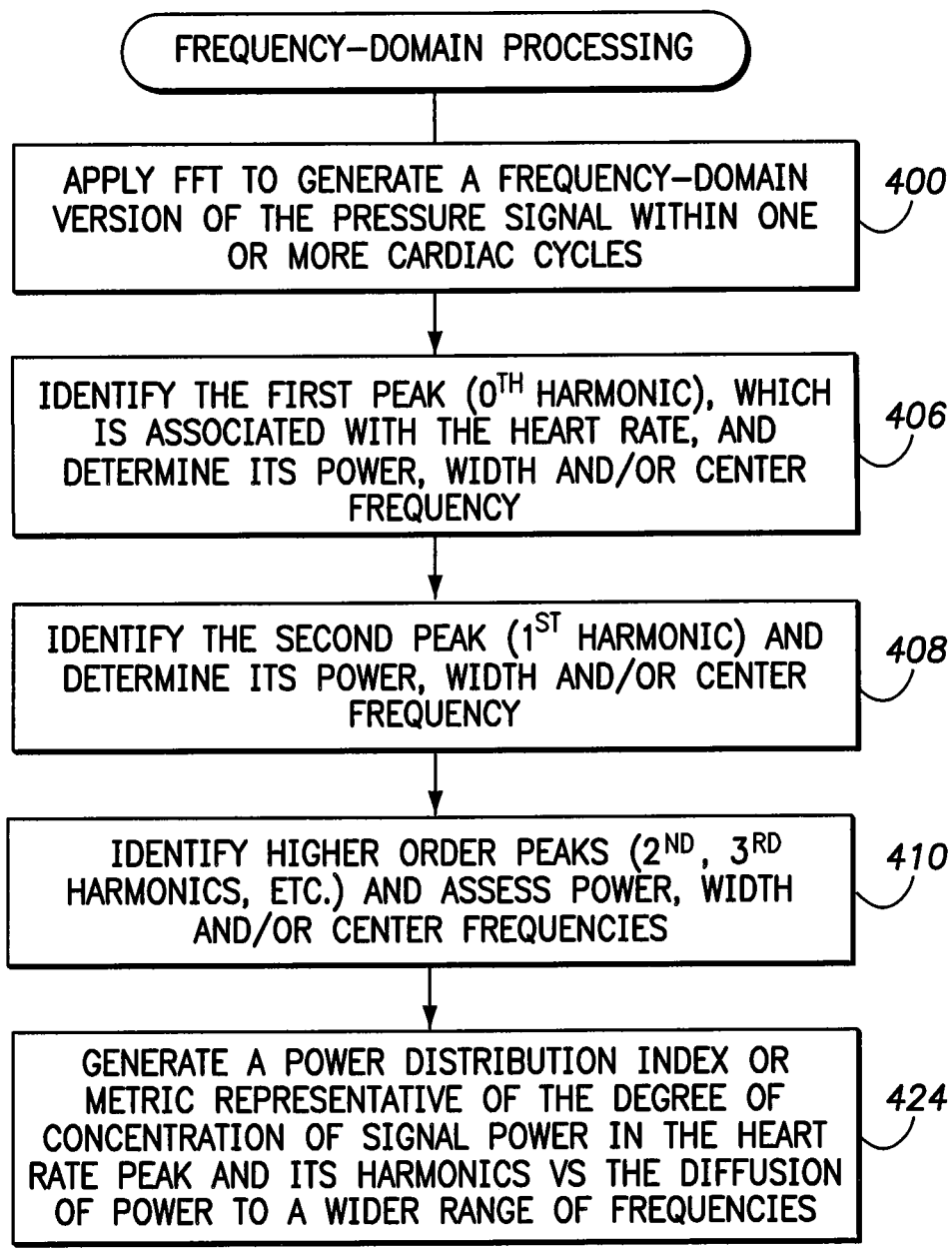
FIG. 7 illustrates frequency-domain processing in greater detail for use with the exemplary detection and discrimination technique of FIG. 3.

Thereafter, based on the shape analysis and the P max location analysis performed at steps 308-330 of FIG. 5, the device then discriminates between hypervolemia (fluid overload) and hypovolemia/euvolemia (i.e. no fluid overload.) More specifically, at step 332, hypervolemia is indicated if (a) the shape index indicates that the pressure signal within the ejection period has a relatively peaked shape and (b) the P max index indicates that the time of P max is relatively early. In this regard, an earlier, sharper peak means the heart may be working disproportionally hard to eject blood against the given afterload, likely due to too high preload. At step 334, hypovolemia/euvolemia is indicated if (a) the shape index indicates that the pressure signal within the ejection period has a relatively more rounded shape and (b) the P max index indicates that the time of P max is relatively late. In circumstances where the indicators might be conflicting, e.g., the shape index indicates possible hypervolemia but the P max index does not, the analysis may be deemed indeterminate pending processing of further pressure signals. Turning now to FIGS. 7 and 8, frequency-domain processing of pressure signals will be described in greater detail.

FIG. 7 illustrates an exemplary frequency-domain processing technique for used in detecting and discriminating euvolemia from hypervolemia and hypovolemia. At step 400, the IMD applies an FFT to generate a frequency-domain representation of the pressure signal within one or more cardiac cycles. FIG. 8 illustrates exemplary frequency spectra graphs generated using an FFT, including a graph 402 based on pressure signals before a fluid overload (i.e. euvolemia) and a graph 404 based on pressure signals during or after a fluid overload (i.e. hypervolemia.) At 406, the device identifies the first peak ($0^{th}$ harmonic) within the frequency-domain representation, which is associated with the heart rate of the patient and determines its power, width and/or center frequency. Width may be assessed, for example based on a full-width half-maximum (FWHM) or other suitable parameters such as the difference of the high and low frequency around the center frequency.) It should be noted that, although spectral width is related to power, these parameters can represent separate metrics. When considering power, the device may be equipped to determine and exploit the power within a predetermined range of the 0th, 1st, and higher harmonics. At 408, the device identifies the second peak ($1^{st}$ harmonic) and determines its power, width and/or center frequency. At 410, the device identifies higher order peaks ($2^{nd}$ harmonic, $3^{rd}$ harmonic, etc.) and determines power, width and/or center frequencies in the higher order peaks. Note that, depending upon the power spectra and the amount of noise in the signal, it might be difficult to specifically identify individual higher order peaks. Nevertheless, the amount of power beyond the $1^{st}$ harmonic can be determined to help assess the distribution of power. Within FIG. 8, the first peak ($0^{th}$ harmonic) is identified in the first graph as peak 412 and in the second graph as peak 414. The second peak ($1^{st}$ harmonic) is identified in the first graph as peak 416 and in the second graph as peak 418. Higher order harmonics are generally identified in the first graph as peaks 420 and in the second graph as peaks 422.

At step 424, the device then generates a power distribution index or metric representative of the degree of concentration of signal power in the heart rate peak and its harmonics versus the diffusion of power to a wider range of frequencies. For example, the device can assess the widths of the heart rate peak and its harmonics and generate a numerical value representative of those widths or may use a separate power metric. A relatively greater width to the heart rate peak and its harmonics is indicative of a diffusion of power consistent with a healthy balance of sympathetic/parasympathetic tone and a healthy degree of heart rate variability (HRV.) A relatively narrower width of the heart rate peak and its harmonics is instead indicative of a concentration of power due to a sympathetic excess and a loss of HRV, which is abnormal. That is, at a fundamental level, the width of the heart beat frequency peak represents the HRV—wider peaks indicate a more normal level of HRV and sympathetic/parasympathetic balance. Conversely, as power converges at a higher heart frequency and its subsequent harmonics, the lower the HRV and thus an imbalance of sympathetic tone.

At step 426, the device compares the power distribution index against a corresponding power distribution threshold to distinguish concentrated power vs. diffused power (and to thereby also assess HRV and sympathetic/parasympathetic balance.) A suitable power distribution threshold (which is a programmable value) can be determined in advance for a particular patient while the patient is known to be euvolemic (e.g. during a post-implant follow-up programming session.) In some examples, the power distribution threshold may be specified in terms of a percentage change in the power distribution index from its euvolemic value. For example, a 10% decrease in the index (i.e. indicating a trend toward increasing power concentration) would indicate possible hypervolemia or hypovolemia and an associated decrease in HRV.

At step 428, the device also compares the center frequency of the heart rate peak (the $0^{th}$ harmonic) determined at step 406 against a corresponding programmable threshold to determine whether the frequency is elevated beyond a euvolemic value and if so, by how much. A suitable threshold can be determined in advance while the patient is known to be euvolemic. In some examples, the threshold may be specified in terms of a percentage change in the center frequency of the first power spectra peak from its euvolemic value. For example, a 10% increase in the center frequency of the first power spectra peak from its euvolemic value would indicate an abnormal volemic state.

Thereafter, based on the power distribution analysis and the frequency shift analysis, the device then discriminates between euvolemia and an abnormal volemic state (i.e. hypervolemia or hypovolemia.) That is, at step 430, hypervolemia/hypovolemia is indicated if (a) the power distribution index indicates that the power is concentrated at the heart rate and its harmonics and (b) the frequency of heart rate peak is elevated. Conversely, at step 432, euvolemia is indicated if (a) the power distribution index indicates that the power is diffused over a wider range of frequencies and (b) the frequency of heart rate peak is not elevated. In circumstances where the indicators might be conflicting, e.g., the power distribution analysis indicates an abnormal state but the frequency shift index indicates a normal state, the analysis may be deemed indeterminate pending processing of further pressure signals. If an abnormal state is detected, the device additionally seeks to determine whether a pressure alternans pattern (or alternating pressure variability pattern) is present. That is, at step 434, the device compares the magnitude (i.e. height) of first order harmonic with the magnitude of heart rate peak ($0^{th}$ harmonic) to detect the ratio therebetween. The higher the ratio of magnitudes, the more likely a pressure alternans pattern is present. That is, if the first harmonic is large in comparison with the zeroth harmonic, then pressure alternans is indicated.

Accordingly, at step 436, if ratio is too high, the device generates an urgent warning of pressure alternans indicative of imminent heart failure decompensation. In this regard, the calculated ratio may be compared against a programmable ratio threshold determined while the patient is known to be euvolemic. A suitable threshold for assessing whether the ratio is too high (indicating pressure alternans) would be in the range of 0.0 and 1.0 (since alternans are basically matched harmonics and so "t" will be between 0.0 and 1.0.) The closer "t" is to 1.0, the more likely alternans are present. More specifically, in some patients, a suitable range for the ratio of 0th to 1st harmonic amplitudes indicating pressure alternans would be 0.85 absolute or an increase of 65%-75% from the baseline (euvolemia) value. For example, any value of the ratio 0th:1st greater than 0.85 would be alarming, as would a change from 0.40 at euvolemia to 0.68 (0.40*1.7) at hypervolemia. (Note that the FFT data of FIG. 8 does not indicate a pressure alternans patterns since the first harmonic is relatively low compared to the zeroth harmonic for both the euvolemic state and the hypervolemic state.) Although the pressure alternans analysis is shown in FIG. 7 as a supplement to the power distribution analysis and the frequency shift analysis, pressure alternans analysis may be made independently. See, FIG. 12, discussed below.

Figure 9:
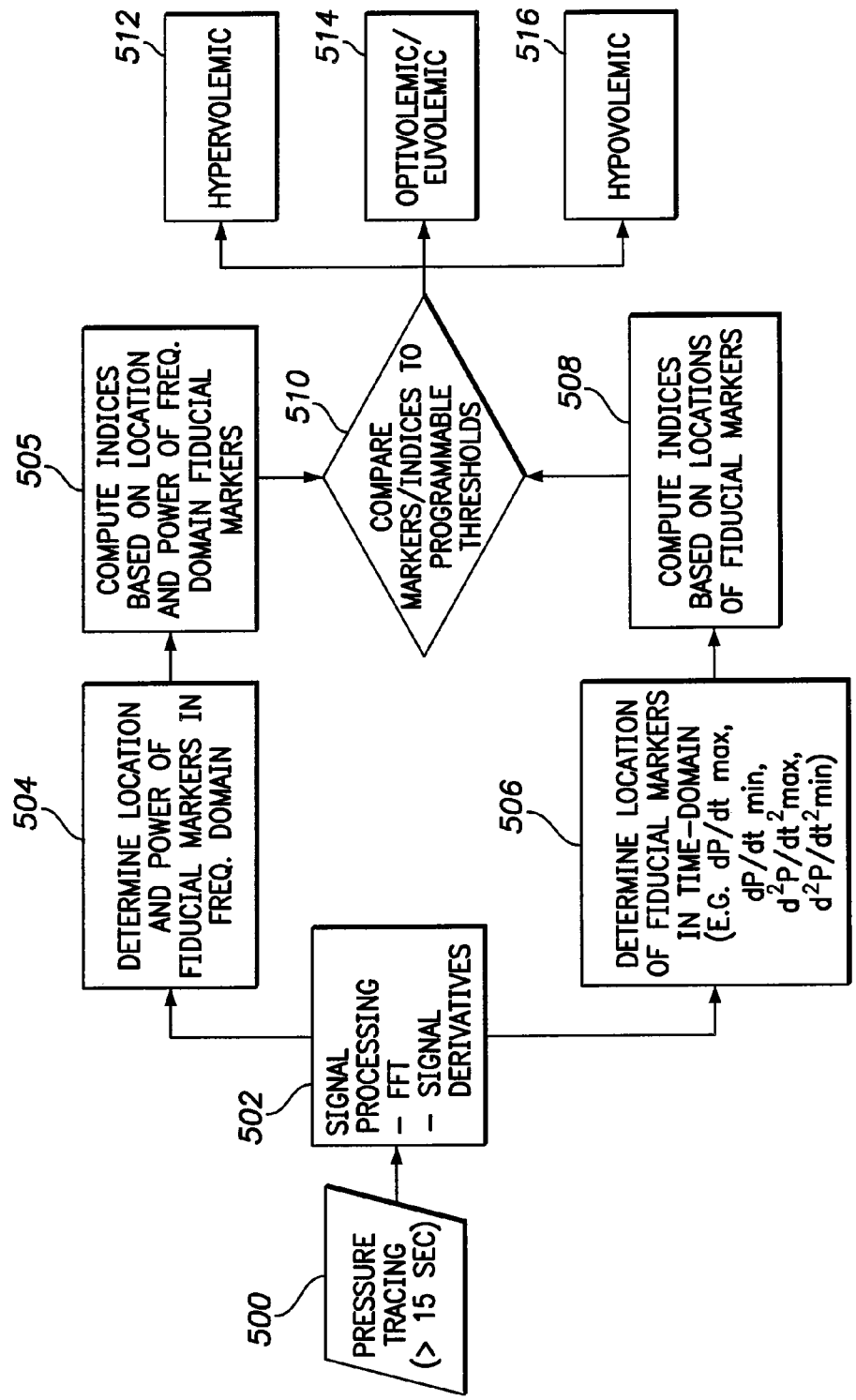
FIG. 9 provides an alternative summary of the techniques for detecting and discriminating hypervolemia, hypovolemia and euvolemia performed by the system of FIG. 1.

FIG. 9 provides an alternative summary of some of the aforementioned techniques. Briefly, at step 500, the implantable device inputs or detects pressure tracings over an interval of at least fifteen seconds and then averages the traces over the cardiac cycles represented therein. At step 502, the device performs initial signal processing by applying the FFT to generate the frequency-domain representation of the pressure signal and by calculating signal derivatives (dP/dt and $d^2P/dt^2$) of the time-domain signal (i.e. the time-varying pressure tracings initially input at step 500.) At step 504, the device determines the location and power of various fiducial markers within the frequency domain. These fiducial markers are the aforementioned power spectra peaks corresponding to the heart rate and its harmonics. At step 505, the device computes indices based on the location and power of the frequency domain fiducial markers. Concurrently, at step 506, the device determines the location of various fiducial markers in the time-domain pressure signal such as the time of P max, dP/dt max, dP/dt min, $d^2P/dt^2$ max and $d^2P/dt^2$ min. At step 508, the device computes the aforementioned indices or metrics based on the fiducial markers such as the P max index and the shape index. At decision block 510, the device compares the various makers and indices against corresponding programmable thresholds to distinguish or discriminate among hypervolemia (512), euvolemia/optivolemia (514) and hypovolemia (516), as already described.

What have been described thus far are various techniques for discriminate among hypervolemia, euvolemia/optivolemia and hypovolemia based time-domain and frequency-domain representations of a cardiac pressure signal. At least some of these techniques can operate independently based either on just the time-domain signals or just the frequency-domain signals to detect or discriminate various conditions. Some of these "stand alone" techniques are summarized in the following section. As the details of these techniques have already been presented above, only general summaries are set forth below.

Stand-Alone Detection and Discrimination Techniques

Figure 10:
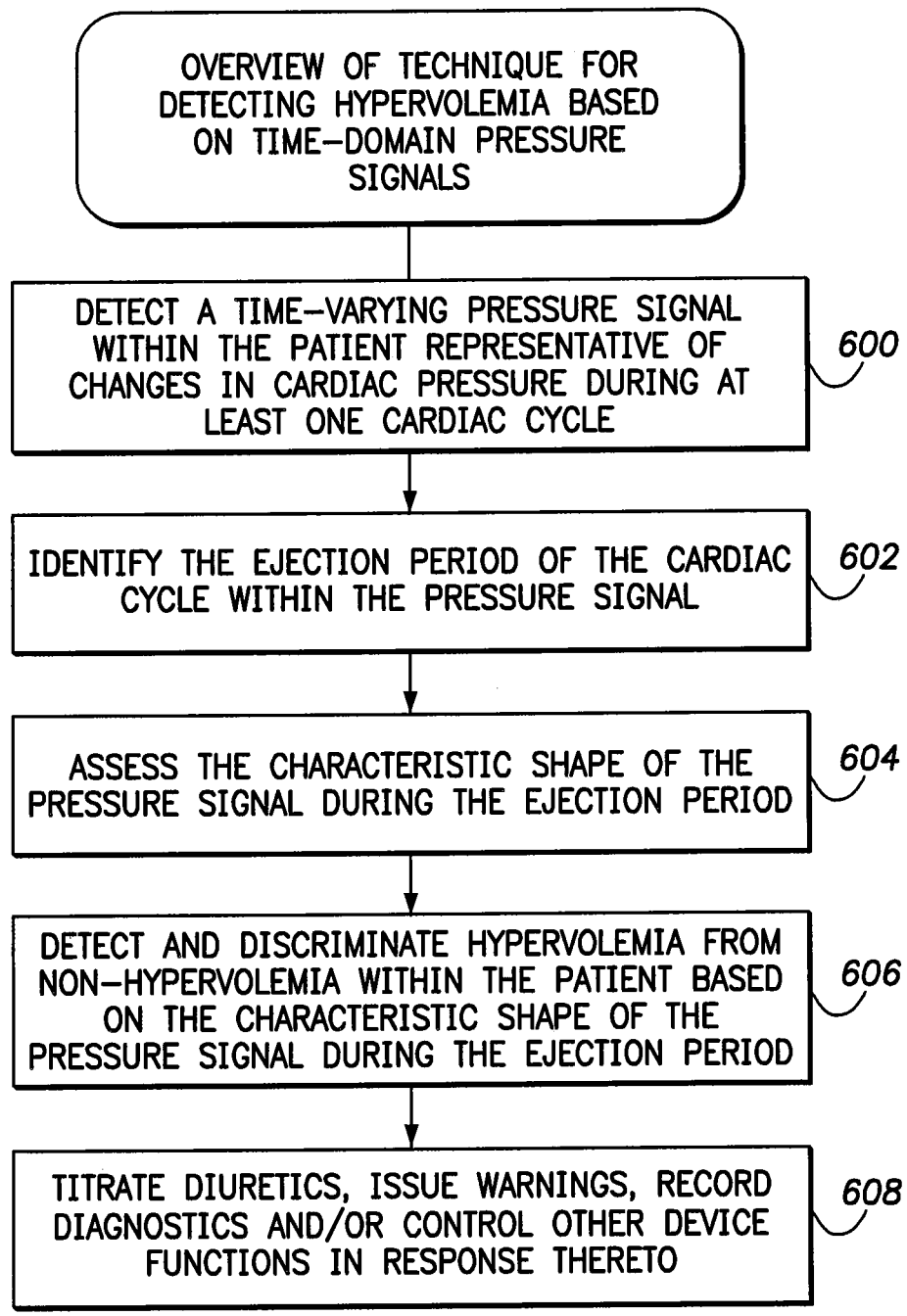
FIG. 10 summarizes techniques for discriminating hypervolemia from non-hypervolemia (i.e. hypovolemia or euvolemia) that may performed by the system of FIG. 1 based on a time-domain signal analysis.

FIG. 10 broadly summarizes a technique for detecting hypervolemia within the patient based on time-varying pressure signals. At step 600, the IMD detects a pressure signal within the patient representative of changes in cardiac pressure during at least one cardiac cycle. At step 602, the device identifies an ejection period of the cardiac cycle within the pressure signal and, at step 604, assesses the characteristic shape of the pressure signal during the ejection period by, e.g., distinguishing between a relatively peaked shape and a relatively rounded shape. At step 606, the device detects and discriminates hypervolemia from non-hypervolemia (i.e. from a lack of hypervolemia) based on the characteristic shape of the pressure signal during the ejection period. At step 608, the device then titrates diuretics, issues warnings, records diagnostics and/or controls other device functions in response thereto, as already discussed.

Figure 11:
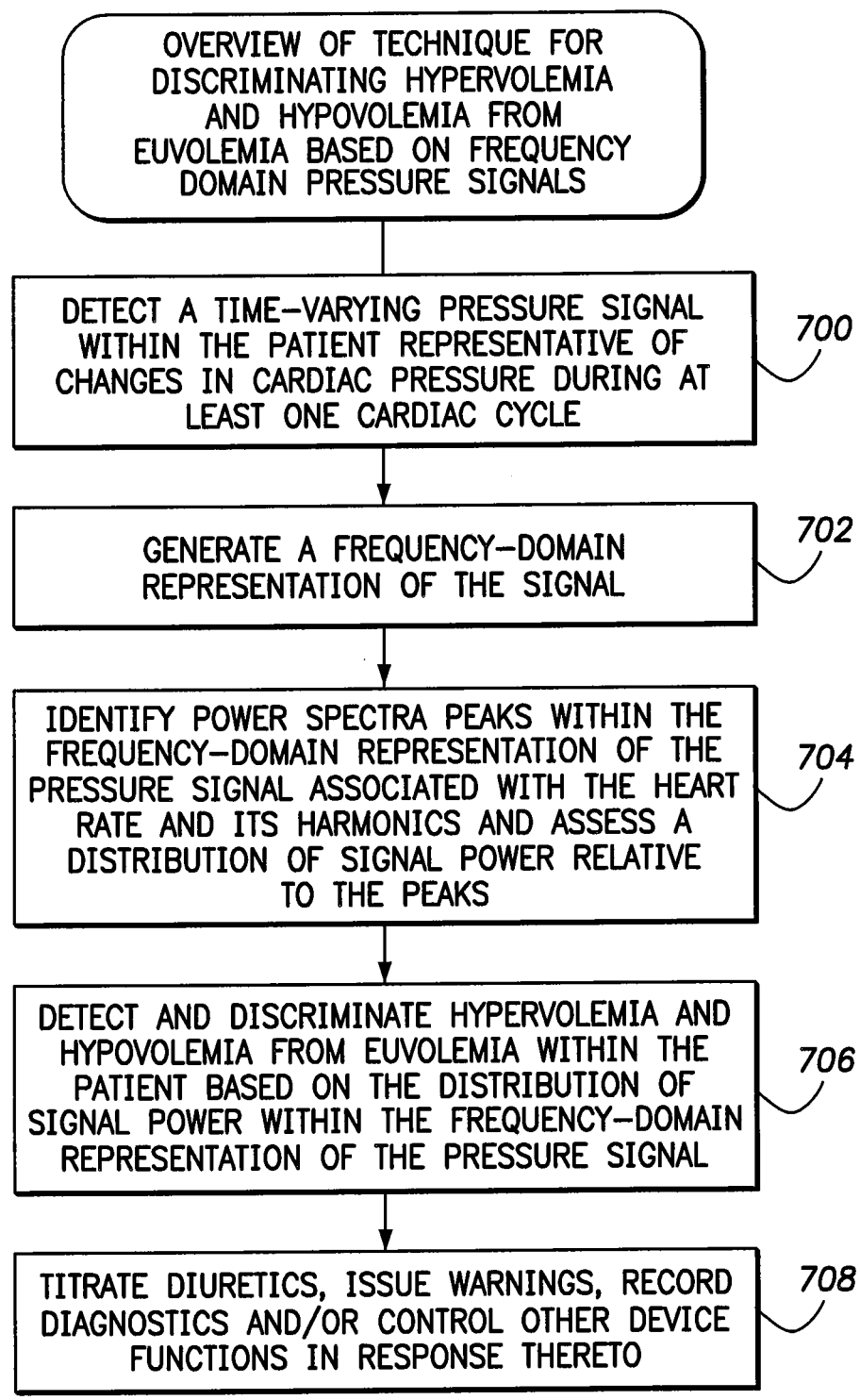
FIG. 11 summarizes techniques for discriminating hypervolemia and hypovolemia from euvolemia that may performed by the system of FIG. 1 based on a frequency-domain signal analysis.

FIG. 11 broadly summarizes the technique for discriminating hypervolemia and hypovolemia from euvolemia within the patient based on frequency-domain pressure signals. At step 700, the IMD detects a pressure signal within the patient representative of changes in cardiac pressure during at least one cardiac cycle. At step 702, the device generates a frequency-domain representation of the pressure signal. At step 704, the device identifies power spectra peaks within the frequency-domain representation of the pressure signal associated with the heart rate and its harmonics and assesses a distribution of signal power relative to the peaks. At step 706, the device detects and discriminates hypervolemia and hypovolemia from euvolemia within the patient based on the distribution of signal power within the frequency-domain representation of the pressure signal. At step 708, the device then titrates diuretics, issues warnings, records diagnostics and/or controls other device functions in response thereto, as already discussed.

Figure 12:
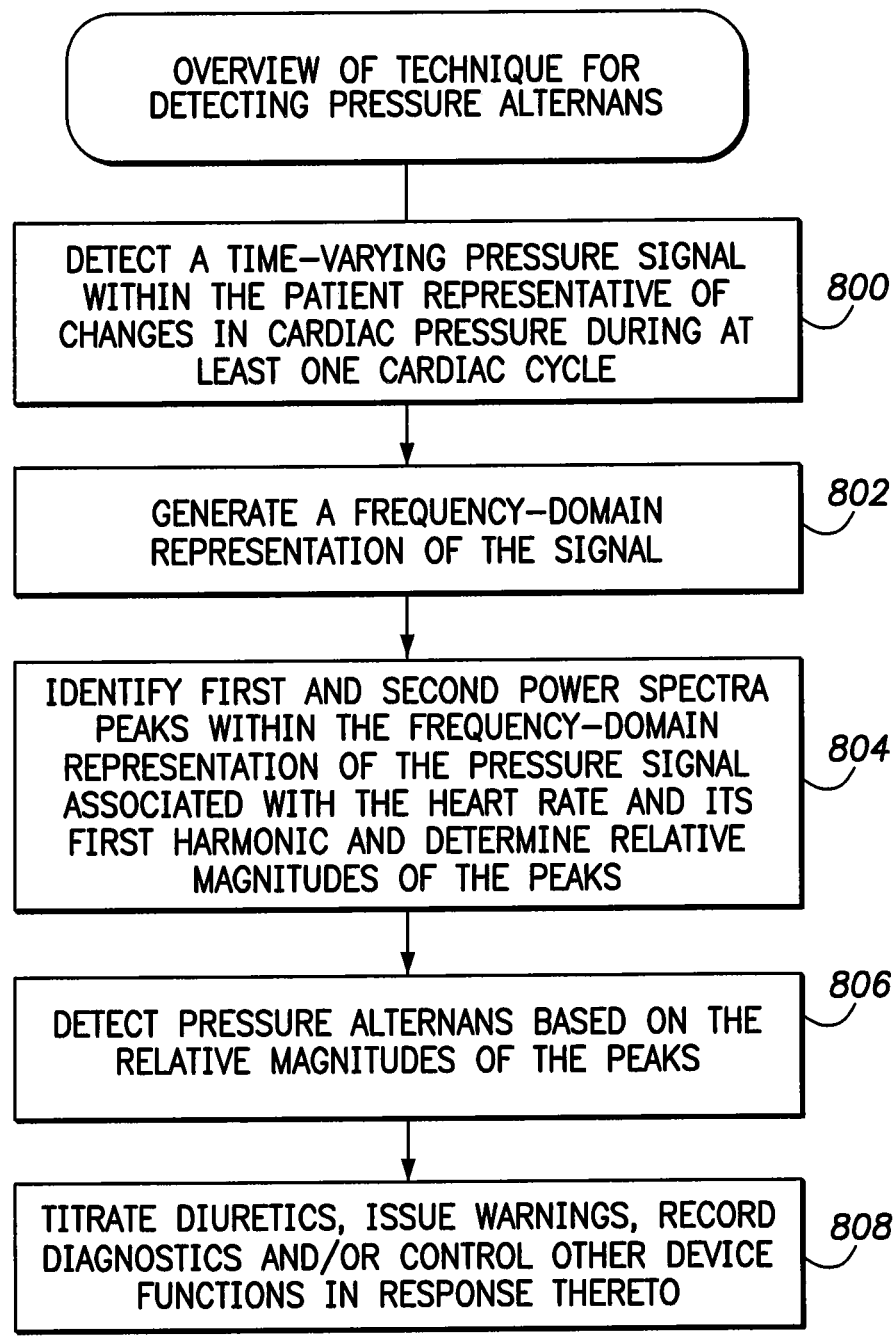
FIG. 12 summarizes techniques for detecting pressure alternans that may performed by the system of FIG. 1 based on a frequency-domain signal analysis.

FIG. 12 broadly summarizes the technique for detecting pressure alternans within the patient based on frequency-domain pressure signals. At step 800, the IMD detects a pressure signal within the patient representative of changes in cardiac pressure during at least one cardiac cycle. At step 802, the device generates a frequency-domain representation of the pressure signal. At step 804, the device identifies power spectra peaks within the frequency-domain representation of the pressure signal associated with the heart rate and its first harmonic and determines the relative magnitude of the two peaks. At step 806, the device detects a pressure alternans pattern (if present) within the patient based on the relative magnitudes of the two peaks (e.g. the ratio of the magnitude of the peak associated with the first harmonic to the magnitude of the peak associated with heart rate.) At step 808, the device then titrates diuretics, issues warnings, records diagnostics and/or controls other device functions in response thereto, as already discussed.

Thus, various techniques have been described for detecting and discriminating various medical conditions within the patient. Depending upon the implementation, these techniques can be exploited alone or in combination with one another or in combination with other detection and discrimination techniques. For example, the implantable device may exploit alternative detection techniques to corroborate a fluid overload detected using the techniques described herein, or the techniques described herein may instead be used to supplement or corroborate detection made using the alternative technique.

Exemplary techniques for detecting a fluid overloads associated with pulmonary edema are discussed in U.S. Pat. No. 7,272,443 to Min et al., entitled "System and Method for Predicting a Heart Condition based on Impedance Values using an Implantable Medical Device." See, also, U.S. Published Patent Application 2010/0069778, of Bornzin et al., entitled "System and Method for Monitoring Thoracic Fluid Levels Based on Impedance Using an Implantable Medical Device," now U.S. Pat. No. 8,032,212 and U.S. Pat. No. 7,628,757 to Koh, entitled "System and Method for Impedance-Based Detection of Pulmonary Edema and Reduced Respiration using an Implantable Medical System." See, also: U.S. Patent Application 2009/0270746 of Min, entitled "Criteria for Monitoring Intrathoracic Impedance," now U.S. Pat. No. 8,452,389 and U.S. Pat. No. 7,574,255, of the same title; U.S. Pat. No. 7,774,055 to Min, entitled "Left Atrial Pressure-Based Criteria for Monitoring Intrathoracic Impedance," and U.S. Patent Application 2010/0305641 of Pillai et al., entitled "System and Method for Detecting Pulmonary Edema based on Impedance Measured using an Implantable Medical Device during a Lead Maturation Interval," now U.S. Pat. No. 8,473,054. Pressure-based techniques for detecting fluid overloads are discussed, e.g., in U.S. Pat. No. 7,946,995 to Koh et al., entitled "Analyzing Circadian Variations of a Hemodynamic Parameter to Determine an Adverse Cardiac Condition."

Exemplary techniques for detecting or trending heart failure are discussed in: U.S. Pat. No. 6,748,261, entitled "Implantable Cardiac Stimulation Device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable Cardiac Stimulation Device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure."

Still further, see the following patents and patent applications: U.S. Patent Application 2008/0288030 to Zhang et al., entitled "Method and Apparatus for Regulating Blood Volume using Volume Receptor Stimulation" and U.S. Patent Application 2007/0065363 of Dalal et al., entitled "Quantifying Hemodynamic Response to Drug Therapy using Implantable Sensor."

For the sake of completeness, a detailed description of an exemplary IMD for performing these techniques will now be provided. However, principles of invention may be implemented within other IMD implementations or within other implantable devices such as stand-alone diagnostic sensors and monitoring devices, ICD devices, CRT-P or CRT-D devices. (A CRT-P is a cardiac resynchronization therapy device with pacing capability. A CRT-D is a cardiac resynchronization therapy device with defibrillation capability.) Furthermore, although examples described herein involve processing of pressure data by the implanted device itself, some operations may be performed using an external device, such as a bedside monitor, device programmer, computer server or other external system. For example, pressure parameters might be transmitted to the external device, which processes the data to detect and discriminate hypervolemia, hypovolemia and euvolemia. Processing by the implanted device itself is preferred as that allows the device to detect abnormal conditions more promptly and to take appropriate action.

Exemplary IMD

FIG. 13 provides a simplified block diagram of the IMD, which in this particular example is a dual-chamber stimulation device capable of treating both fast and slow arrhythmias with stimulation therapy, including cardioversion, defibrillation, and pacing stimulation, as well as capable of performing the pulmonary fluid monitoring functions described above. To provide atrial chamber pacing stimulation and sensing, IMD 10 is shown in electrical communication with a heart 912 by way of a left atrial lead 920 having an atrial tip electrode 922 and an atrial ring electrode 923 implanted in the atrial appendage. IMD 10 is also in electrical communication with the heart by way of a right ventricular lead 930 having, in this embodiment, a ventricular tip electrode 932, a right ventricular ring electrode 934, a right ventricular (RV) coil electrode 936, and a superior vena cava (SVC) coil electrode 938. Typically, the right ventricular lead 930 is transvenously inserted into the heart so as to place the RV coil electrode 936 in the right ventricular apex, and the SVC coil electrode 938 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, IMD 10 is coupled to a "coronary sinus" lead 924 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 924 is designed to receive atrial and ventricular cardiac signals and to deliver left ventricular pacing therapy using at least a left ventricular tip electrode 926, left atrial pacing therapy using at least a left atrial ring electrode 927, and shocking therapy using at least a left atrial coil electrode 928. With this configuration, biventricular pacing can be performed. A pressure transducer (such as an LAP sensor) is shown mounted adjacent the left atria along lead 924. This location is merely illustrative. The actual location of the pressure transducer may differ, depending upon whether it is intended to sense LAP, LVP, PAP or other pertinent pressure signals or proxies.

Although only three leads are shown in FIG. 13, it should also be understood that additional stimulation leads (with one or more pacing, sensing and/or shocking electrodes) might be used in order to efficiently and effectively provide pacing stimulation to the left side of the heart or atrial cardioversion and/or defibrillation.

Figure 14:
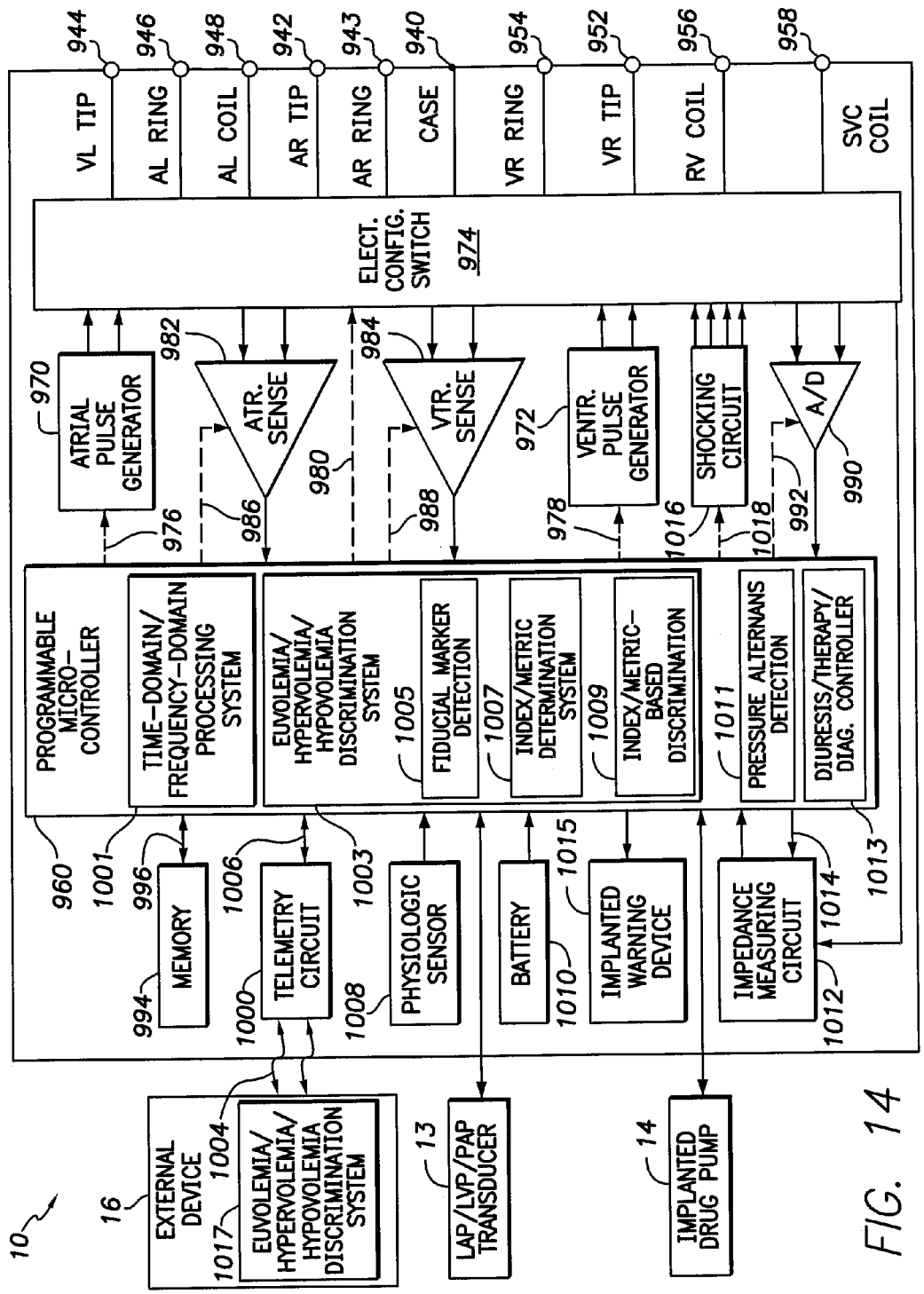
FIG. 14 is a functional block diagram of the device of FIG. 13, illustrating basic circuit elements that provide cardioversion, defibrillation and/or pacing stimulation in the heart and particularly illustrating components for controlling or implementing the techniques of FIGS. 2-12.

A simplified block diagram of internal components of IMD 10 is shown in FIG. 14. While a particular IMD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned impedance-based functions.

The housing 940 for IMD 10, shown schematically in FIG. 14, is often referred to as the "can", "case" or "case electrode" and may be programmably selected to act as the return electrode for all "unipolar" modes. The housing 940 may further be used as a return electrode alone or in combination with one or more of the coil electrodes, 928, 936 and 938, for shocking purposes. The housing 940 further includes a connector (not shown) having a plurality of terminals, 942, 943, 944, 946, 948, 952, 954, 956 and 958 (shown schematically and, for convenience, the names of the electrodes to which they are connected are shown next to the terminals). As such, to achieve right atrial sensing and pacing, the connector includes at least a right atrial tip terminal ($A_R$ TIP) 942 adapted for connection to the atrial tip electrode 922 and a right atrial ring ($A_R$ RING) electrode 943 adapted for connection to right atrial ring electrode 923. To achieve left chamber sensing, pacing and shocking, the connector includes at least a left ventricular tip terminal ($V_L$ TIP) 944, a left atrial ring terminal ($A_L$ RING) 946, and a left atrial shocking terminal ($A_L$ COIL) 948, which are adapted for connection to the left ventricular ring electrode 926, the left atrial tip electrode 927, and the left atrial coil electrode 928, respectively. To support right chamber sensing, pacing and shocking, the connector further includes a right ventricular tip terminal ($V_R$ TIP) 952, a right ventricular ring terminal ($V_R$ RING) 954, a right ventricular shocking terminal ($R_V$ COIL) 956, and an SVC shocking terminal (SVC COIL) 958, which are adapted for connection to the right ventricular tip electrode 932, right ventricular ring electrode 934, the RV coil electrode 936, and the SVC coil electrode 938, respectively. Although not shown, additional terminals may be needed for use with pressure transducer 13 and drug pump 14.

At the core of IMD 10 is a programmable microcontroller 960, which controls the various modes of stimulation therapy. As is well known in the art, the microcontroller 960 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 960 includes the ability to process or monitor input signals (data) as controlled by a program code stored in a designated block of memory. The details of the design and operation of the microcontroller 960 are not critical to the invention. Rather, any suitable microcontroller 960 may be used that carries out the functions described herein. The use of microprocessor-based control circuits for performing timing and data analysis functions are well known in the art.

As shown in FIG. 14, an atrial pulse generator 970 and a ventricular/impedance pulse generator 972 generate pacing stimulation pulses for delivery by the right atrial lead 920, the right ventricular lead 930, and/or the coronary sinus lead 924 via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, combipolar, etc.) by selectively closing the appropriate combination of switches (not shown) as is known in the art.

Atrial sensing circuits 982 and ventricular sensing circuits 984 may also be selectively coupled to the right atrial lead 920, coronary sinus lead 924, and the right ventricular lead 930, through the switch 974 for detecting the presence of cardiac activity in each of the four chambers of the heart. Accordingly, the atrial (ATR. SENSE) and ventricular (VTR. SENSE) sensing circuits, 982 and 984, may include dedicated sense amplifiers, multiplexed amplifiers or shared amplifiers. The switch 974 determines the "sensing polarity" of the cardiac signal by selectively closing the appropriate switches, as is also known in the art. In this way, the clinician may program the sensing polarity independent of the stimulation polarity. Each sensing circuit, 982 and 984, preferably employs one or more low power, precision amplifiers with programmable gain and/or automatic gain control, bandpass filtering, and a threshold detection circuit, as known in the art, to selectively sense the cardiac signal of interest. The automatic gain control enables IMD 10 to deal effectively with the difficult problem of sensing the low amplitude signal characteristics of atrial or ventricular fibrillation. The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity in the appropriate chambers of the heart.

For arrhythmia detection, IMD 10 utilizes the atrial and ventricular sensing circuits, 982 and 984, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 960 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 990. The data acquisition system 990 is configured to acquire intracardiac electrogram signals, convert the raw analog data into a digital signal, and store the digital signals for later processing and/or telemetric transmission to an external device 1002. The data acquisition system 990 is coupled to the right atrial lead 920, the coronary sinus lead 924, and the right ventricular lead 930 through the switch 974 to sample cardiac signals across any pair of desired electrodes. The microcontroller 960 is further coupled to a memory 994 by a suitable data/address bus 996, wherein the programmable operating parameters used by the microcontroller 960 are stored and modified, as required, in order to customize the operation of IMD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable IMD 10 may be non-invasively programmed into the memory 994 through a telemetry circuit 1000 in telemetric communication with the external device 1002, such as a programmer, transtelephonic transceiver or a diagnostic system analyzer. The telemetry circuit 1000 is activated by the microcontroller by a control signal 1006. The telemetry circuit 1000 advantageously allows intracardiac electrograms and status information relating to the operation of IMD 10 (as contained in the microcontroller 960 or memory 994) to be sent to the external device 1002 through an established communication link 1004. IMD 10 further includes an accelerometer or other physiologic sensor 1008, commonly referred to as a "rate-responsive" sensor because it is typically used to adjust pacing stimulation rate according to the exercise state of the patient. However, the physiological sensor 1008 may further be used to detect changes in cardiac output, changes in the physiological condition of the heart, or diurnal changes in activity (e.g., detecting sleep and wake states) and to detect arousal from sleep. Additionally, sensor 1008 could be equipped to detect pulmonary fluid levels or proxies for pulmonary fluid levels. Accordingly, the microcontroller 960 responds by adjusting the various pacing parameters (such as rate, AV Delay, V-V Delay, etc.) at which the atrial and ventricular pulse generators, 970 and 972, generate stimulation pulses. While shown as being included within IMD 10, it is to be understood that the physiologic sensor 1008 may also be external to IMD 10, yet still be implanted within or carried by the patient. A common type of rate responsive sensor is an activity sensor incorporating an accelerometer or a piezoelectric crystal, which is mounted within the housing 940 of IMD 10. Other types of physiologic sensors are also known, for example, sensors that sense the oxygen content of blood, respiration rate and/or minute ventilation, pH of blood, ventricular gradient, pulmonary artery pressure, etc.

The IMD additionally includes a battery 1010, which provides operating power to all of the circuits shown in FIG. 14. The battery 1010 may vary depending on the capabilities of IMD 10. If the system only provides low voltage therapy, a lithium iodine or lithium copper fluoride cell may be utilized. For IMD 10, which employs shocking therapy, the battery 1010 must be capable of operating at low current drains for long periods, and then be capable of providing high-current pulses (for capacitor charging) when the patient requires a shock pulse. The battery 1010 must also have a predictable discharge characteristic so that elective replacement time can be detected. Accordingly, IMD 10 is preferably capable of high voltage therapy and appropriate batteries.

As further shown in FIG. 14, IMD 10 is shown as having an impedance measuring circuit 1012, which is enabled by the microcontroller 960 via a control signal 1014. Herein, impedance is primarily detected for use in evaluating thoracic and cardiogenic impedance for use in evaluating thoracic fluids. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 1012 is advantageously coupled to the switch 974 so that any desired electrode may be used.

In the case where IMD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 960 further controls a shocking circuit 1016 by way of a control signal 1018. The shocking circuit 1016 generates shocking pulses of low (up to 0.5 joules), moderate (0.5-10 joules) or high energy (11 to 40 joules or more), as controlled by the microcontroller 960. Such shocking pulses are applied to the heart of the patient through at least two shocking electrodes, and as shown in this embodiment, selected from the left atrial coil electrode 928, the RV coil electrode 936, and/or the SVC coil electrode 938. The housing 940 may act as an active electrode in combination with the RV electrode 936, or as part of a split electrical vector using the SVC coil electrode 938 or the left atrial coil electrode 928 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 9-40 joules or more), delivered asynchronously (since R-waves may be too disorganized), and pertaining exclusively to the treatment of fibrillation. Accordingly, the microcontroller 960 is capable of controlling the synchronous or asynchronous delivery of the shocking pulses.

Microcontroller 960 also includes various components directed to implementing the aforementioned detecting and discrimination methods. More specifically, an on-board time-domain/frequency-domain processing system 1001 is operative to generate separate time-domain and frequency-domain representations of a pressure signal received from pressure transducer 13. A euvolemia/hypervolemia/hypovolemia discrimination system 1003 is operative to discriminate among euvolemia, hypervolemia and hypovolemia within the patient based on an analysis of the separate time-domain and frequency-domain representations of the pressure signal. The discrimination system includes a fiducial marker detection system 1005 operative to detect the various fiducial makers discussed above, such as dP/dt max and dP/dt min. An index/metric determination system 1007 is operative to determine the various indices and metrics discussed above such as the shape index and the P max location index and the likelihood index. An index/metric-based discrimination system 1009 is operative to detect and discriminate euvolemia, hypervolemia and hypovolemia based on the various fiducial markers and indices as already described. The microcontroller also includes a pressure alternans detection system 1011 operative to detect a pressure alternans pattern.

A diuresis/therapy/diagnostics controller 1013 controls generation of diagnostic data and warning signals in response to detect of any abnormal conditions. Diagnostic data is stored within memory 994. Warning signals may be relayed to the patient via implanted warning device 1015 or external device 16. Controller 1013 also controls and titrates the delivery of diuretics (or other appropriate therapies) using drug pump 14 as described above (if one is implanted.) In implementations where there is no drug pump, titration of diuretics is typically achieved by instead providing suitable instructions to the patient or caregiver via the bedside monitor (or other external device.)

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein may be performed by, or under the control of, an external device. Accordingly, external device 16 is shown to include a euvolemia/hypervolemia/hypovolemia discrimination system 1017 operative to detect and discriminate euvolemia, hypervolemia, hypovolemia, as well as to detect pressure alternans patterns, based on pressure signals or other parameters sent from the implanted device. In general, any of the components shown within the microcontroller 960 may have corresponding components within the external device. Still further, the external device may include components for setting or adjusting the various programmable thresholds discussed above.

What have been described are various systems and methods for use with an IMD or diagnostic sensor. However, principles of the invention may be exploiting using other implantable medical systems. Thus, while the invention has been described with reference to particular exemplary embodiments, modifications can be made thereto without departing from the scope of the invention.

What is claimed is:

1. A method for use with an implantable medical device for implant within a patient, the method comprising:
   applying a cardiac pressure detector to detect a pressure signal within the patient representative of changes in cardiac pressure during at least one cardiac cycle;
   applying a time-domain and frequency-domain processor to generate separate time-domain and frequency-domain representations of the pressure signal;
   applying a discrimination system to discriminate among euvolemia, hypervolemia and hypovolemia within the patient based on the time-domain and the frequency-domain representations of the pressure signal;
   wherein applying a discrimination system to discriminate euvolemia, hypervolemia and hypovolemia comprises:
      identifying an ejection period of the cardiac cycle within the time-domain representation of the pressure signal;
      assessing a shape of the time-domain representation of the pressure signal during the ejection period; and
      discriminating hypervolemia from hypovolemia and euvolemia based on the shape of the time-domain representation of the pressure signal during the ejection period; and
   applying a controller unit to control at least one implantable medical device therapeutic function in response to applying a discrimination system to discriminate among euvolemia, hypervolemia and hypovolemia.

2. The method of claim 1 wherein applying a discrimination system to discriminate hypervolemia from hypovolemia and euvolemia comprises:
   generating an indication of hypervolemia if the time-domain representation of the pressure signal during the ejection period has a peaked shape; and
   generating an indication of lack of hypervolemia if the time-domain representation of the pressure signal during the ejection period has a more rounded shape.

3. The method of claim 1 wherein identifying the ejection period comprises:
   determining first order derivatives (dP/dt) and second order derivatives ($d^2P/dt^2$) of the time-domain representation of the pressure signal;

identifying fiducial markers within the time-domain representation of the pressure signals based on the first and second order derivatives including: a maximum magnitude of dP/dt (dP/dt max); a time of dP/dt max; a minimum magnitude of dP/dt (dP/dt min); a time of dP/dt min; a peak magnitude of the pressure (P max); a time of P max; and a minimum magnitude of $d^2P/dt^2$; and identifying the ejection period as the interval between the time of minimum $d^2P/dt^2$ after dP/dt max and the time of minimum $d^2P/dt^2$ before dP/dt min.

4. The method of claim 1 wherein assessing the shape of the time-domain representation of the pressure signal during the ejection period comprises generating a shape index representative of a degree of roundness to the time domain representation of the pressure signal during the ejection period.

5. The method of claim 4 wherein the shape index is generated based on one or more of a best-fit quadratic curve or a best-fit cosine curve.

6. A method for use with an implantable medical device for implant within a patient, the method comprising:
applying a cardiac pressure detector to detect a pressure signal within the patient representative of changes in cardiac pressure during at least one cardiac cycle;
applying a time-domain and frequency-domain processor to generate separate time-domain and frequency-domain representations of the pressure signal; and
applying a discrimination system to discriminate among euvolemia, hypervolemia and hypovolemia within the patient based on the time-domain and the frequency-domain representations of the pressure signal;
wherein applying a discrimination system to discriminate euvolemia, hypervolemia and hypovolemia comprises:
identifying a maximum rate of change (dP/dt max) of the time domain representation of the pressure signal;
identifying a minimum rate of change (dP/dt min) of the time domain representation of the pressure signal;
identifying a maximum pressure value (P max) within the time domain representation of the pressure signal;
determining a time of P max relative to dP/dt max and dP/dt min; and
discriminating hypervolemia from hypovolemia and euvolemia based on the time of P max relative to dP/dt max and dP/dt min; and
applying a controller unit to control at least one implantable medical device therapeutic function in response to applying a discrimination system to discriminate among euvolemia, hypervolemia and hypovolemia.

7. The method of claim 6 wherein applying a discrimination system to discriminate hypervolemia from hypovolemia and euvolemia comprises:
generating an indication of hypervolemia if P max is early; and
generating an indication of lack of hypervolemia if P max is late.

8. A method for use with an implantable medical device for implant within a patient, the method comprising:
applying a cardiac pressure detector to detect a pressure signal within the patient representative of changes in cardiac pressure during at least one cardiac cycle;
applying a time-domain and frequency-domain processor to generate separate time-domain and frequency-domain representations of the pressure signal; and
applying a discrimination system to discriminate among euvolemia, hypervolemia and hypovolemia within the patient based on the time-domain and the frequency-domain representations of the pressure signal;
wherein applying a discrimination system to discriminate euvolemia, hypervolemia and hypovolemia comprises:
identifying power spectra peaks within the frequency-domain representation of the pressure signals associated with the heart rate and its harmonics;
assessing a distribution of signal power relative to the peaks; and
discriminating euvolemia from hypovolemia and hypervolemia based on the distribution of signal power relative to the peaks; and
applying a controller unit to control at least one implantable medical device therapeutic function in response to applying a discrimination system to discriminate among euvolemia, hypervolemia and hypovolemia.

9. The method of claim 8 wherein applying a discrimination system to discriminate euvolemia from hypovolemia and hypervolemia comprises:
generating an indication of euvolemia if signal power is diffused from the peaks; and
generating an indication of an abnormal volemic state if the signal power is concentrated at the power spectra peaks.

10. The method of claim 8 wherein assessing the distribution of signal power comprises determining widths of the power spectra peaks and associating narrow widths with a concentration of power and associating greater widths with a diffusion of power.

11. A method for use with an implantable medical device for implant within a patient, the method comprising:
applying a cardiac pressure detector to detect a pressure signal within the patient representative of changes in cardiac pressure during at least one cardiac cycle;
applying a time-domain and frequency-domain processor to generate separate time-domain and frequency-domain representations of the pressure signal; and
applying a discrimination system to discriminate among euvolemia, hypervolemia and hypovolemia within the patient based on the time-domain and the frequency-domain representations of the pressure signal;
wherein applying a discrimination system to discriminate euvolemia, hypervolemia and hypovolemia comprises:
identifying a first power spectra peak within the frequency-domain representation of the pressure signals associated with heart rate;
determining a frequency of the first power spectra peak;
associating a higher frequency of the first power spectra peak with hypervolemia; and
associating a lower frequency of the heart rate peak with a lack of hypervolemia; and
applying a controller unit to control at least one implantable medical device therapeutic function in response to applying a discrimination system to discriminate among euvolemia, hypervolemia and hypovolemia.

12. A method for use with an implantable medical device for implant within a patient, the method comprising:
applying a cardiac pressure detector to detect a pressure signal within the patient representative of changes in cardiac pressure during at least one cardiac cycle;
applying a time-domain and frequency-domain processor to generate separate time-domain and frequency-domain representations of the pressure signal; and
applying a discrimination system to discriminate among euvolemia, hypervolemia and hypovolemia within the patient based on the time-domain and the frequency-domain representations of the pressure signal;
wherein applying a discrimination system to discriminate euvolemia, hypervolemia and hypovolemia comprises:

identifying first and second power spectra peaks within the frequency-domain representation of the pressure signals;

determining relative magnitudes of the first and second peaks; and detecting pressure alternans based on the relative magnitudes of the first and second peaks; and applying a controller unit to control at least one implantable medical device therapeutic function in response to applying a discrimination system to discriminate among euvolemia, hypervolemia and hypovolemia.

13. The method of claim 12 wherein detecting pressure alternans based on the relative magnitudes of the first and second peaks comprises:

determining a ratio of the magnitude of the second peak to the first peak; and detecting pressure alternans if the ratio exceeds a threshold indicative of pressure alternans.

14. The method of claim 13 further comprising generating a warning indicative of heart failure decompensation in response to detection of pressure alternans.

15. A method for use with an implantable medical device for implant within a patient, the method comprising:

applying a cardiac pressure detector to detect a pressure signal within the patient representative of changes in cardiac pressure during at least one cardiac cycle;

applying a time-domain and frequency-domain processor to generate separate time-domain and frequency-domain representations of the pressure signal; and applying a discrimination system to discriminate among euvolemia, hypervolemia and hypovolemia within the patient based on the time-domain and the frequency-domain representations of the pressure signal;

wherein applying a discrimination system to discriminate among euvolemia, hypervolemia and hypovolemia comprises:

identifying an ejection period of the cardiac cycle within the time-domain representation of the pressure signals and assessing a characteristic shape of the pressure signal during the ejection period;

identifying power spectra peaks within the frequency-domain representation of the pressure signals associated with the heart rate and its harmonics and assessing a distribution of signal power relative to the peaks;

detecting hypervolemia based on a peaked shape to the time-domain representation of the pressure signal during the ejection period along with a concentration of signal power at the power spectra peaks of the frequency-domain representation of the pressure signal;

detecting hypovolemia based on a rounded shape to the time-domain representation of the pressure signal during the ejection period along with a concentration of signal power at the power spectra peaks of the frequency-domain representation of the pressure signal; and detecting euvolemia based on a rounded shape to the time-domain representation of the pressure signal during the ejection period along with a more diffused signal power within the frequency-domain representation of the pressure signal; and applying a controller unit to control at least one implantable medical device therapeutic function in response to applying a discrimination system to discriminate among euvolemia, hypervolemia and hypovolemia.

* * * * *